US006936289B2

(12) United States Patent
Olsen et al.

(10) Patent No.: US 6,936,289 B2
(45) Date of Patent: Aug. 30, 2005

(54) METHOD OF IMPROVING THE PROPERTIES OF A FLOUR DOUGH, A FLOUR DOUGH IMPROVING COMPOSITION AND IMPROVED FOOD PRODUCTS

(75) Inventors: Torkil Steenholt Olsen, Morelos (MX); Inge Lise Povlsen, Skanderborg (DK); Jorn Borch Soe, Tilst (DK); Charlotte Horsmans Poulsen, Brabrand (DK); Pernille Bak Hostrup, Mårslet (DK)

(73) Assignee: Danisco A/S, Copenhagen (DK)

( * ) Notice: Subject to any disclaimer, the term of this patent is extended or adjusted under 35 U.S.C. 154(b) by 99 days.

(21) Appl. No.: 10/260,578

(22) Filed: Oct. 1, 2002

(65) Prior Publication Data

US 2003/0194467 A1 Oct. 16, 2003

Related U.S. Application Data

(63) Continuation-in-part of application No. 09/932,923, filed on Aug. 21, 2001, now Pat. No. 6,726,942, which is a continuation of application No. 08/676,186, filed on Sep. 12, 1996, now Pat. No. 6,358,543, which is a continuation-in-part of application No. 08/483,870, filed on Jun. 7, 1995, now abandoned, said application No. 10/260,578, is a continuation-in-part of application No. 10/040,394, filed on Jan. 9, 2002, which is a division of application No. 09/402,664, filed on Oct. 22, 1999, now Pat. No. 6,406,723, said application No. 10/260,578, is a continuation-in-part of application No. 10/150,429, filed on May 17, 2002.

(60) Provisional application No. 60/347,007, filed on Jan. 9, 2002, and provisional application No. 60/398,020, filed on Jul. 24, 2002.

(30) Foreign Application Priority Data

Jun. 4, 1996 (WO) ............................... PCT/DK96/00239
Apr. 9, 1997 (DK) ............................................... 0400/97
Apr. 3, 1998 (WO) ............................... PCT/DK98/00136
May 18, 2001 (GB) ............................................... 0112226
May 24, 2002 (GB) ............................................... 0211975

(51) Int. Cl.$^7$ ................................................. A21D 2/00
(52) U.S. Cl. ........................................ 426/20; 426/549
(58) Field of Search .......................... 426/20, 549, 555

(56) References Cited

U.S. PATENT DOCUMENTS

| 2,783,150 | A | 2/1957 | Luther |
| 3,520,702 | A | 7/1970 | Merzi |
| 5,059,430 | A | 10/1991 | Bowles |
| 5,094,951 | A | 3/1992 | Rosenberg |
| 5,108,765 | A | 4/1992 | Maat et al. |
| 5,318,785 | A | 6/1994 | DeStefanis |
| 5,451,413 | A | 9/1995 | Fok et al. |
| 5,650,188 | A | 7/1997 | Gaubert et al. |
| 5,916,607 | A | 6/1999 | Mutsaers et al. |
| 6,039,983 | A | 3/2000 | Wagner et al. |
| 6,251,626 | B1 | 6/2001 | Stougaard et al. |
| 6,358,543 | B1 | 3/2002 | S.o slashed.e et al. |
| 6,406,723 | B1 | 6/2002 | S.o slashed.e et al. |

FOREIGN PATENT DOCUMENTS

| CA | 2012723 | 9/1990 |
| CA | 2102723 | 9/1990 |
| CA | 2134597 | 4/1995 |
| CA | 2151978 | 12/1995 |
| CA | 2157718 | 3/1996 |
| CA | 2224143 | 12/1996 |
| CL | 858-1991 | 3/1992 |
| CL | 1376-1992 | 9/1993 |
| CL | 39483 | 9/1994 |
| CL | 1363-95 | 9/1994 |
| CL | 875-95 | 6/1995 |
| CL | 1595-1994 | 4/1996 |
| CL | 875-1994 | 5/1996 |
| CL | 1363-1995 | 8/1996 |
| DE | A1050703 | 3/1956 |
| DE | 4301904 A1 | 2/1994 |
| DE | 4301904 | 2/1994 |
| EP | 0010296 | 12/1982 |
| EP | B1-321-811 | 6/1989 |
| EP | B1-338-452 | 10/1989 |
| EP | A0468731 | 7/1991 |
| EP | 0468731 | 1/1992 |
| EP | 0396 162 | 1/1993 |
| EP | 0585988 B1 | 9/1994 |
| EP | WO A9501727 | 1/1995 |
| EP | 0 682 116 | 11/1995 |
| EP | WO 95129996 | 11/1995 |
| GB | 2358784 | 8/2001 |
| JP | 73016612 | 12/1970 |
| JP | 61085158 | 4/1986 |
| JP | 03164127 | 7/1991 |
| JP | A92084848 | 3/1992 |
| JP | 04-200339 | 7/1992 |
| JP | 04207145 | 7/1992 |
| JP | 04207146 A | 7/1992 |
| JP | 1994000010444 | 1/1994 |
| JP | A6296467 | 10/1994 |

(Continued)

OTHER PUBLICATIONS

Sullivan, James Denis Jr., Diss. Abstr. Int. B, 1973, 34(5), 1875, CAN 80: 105204 AN 1974: 105204 CAPLUS, "Purification and characterization of hexose oxidase from the red alga *Chondrus crispus*".

Groen, B. W., s De Vries, J. A. Duine (1997), Eu. J. Biochem., vol. 244, pp. 858–861, "Characterization of hexose from the red seaweed *Chondrus crispus*".

(Continued)

Primary Examiner—Keith Hendricks
(74) Attorney, Agent, or Firm—Steptoe & Johnson LLP

(57) ABSTRACT

A method of improving the rheological and/or machineability properties of a flour dough and/or the quality of the product made from the dough, comprising adding to the dough a combination comprising a Hox and an emulsifying agent.

45 Claims, 1 Drawing Sheet

FOREIGN PATENT DOCUMENTS

| | | |
|---|---|---|
| JP | 06-296467 | 10/1994 |
| JP | 1994000010444 | 10/1994 |
| JP | 7 274807 | 10/1995 |
| JP | 7 274807 A | 10/1995 |
| JP | 07274807 | 10/1995 |
| JP | 07274807 A | 10/1995 |
| JP | 03164127 | 7/1999 |
| JP | 04207145 | 7/1999 |
| JP | 04207146 A | 7/1999 |
| WO | WO 94/04035 | 3/1994 |
| WO | WO 96/39851 | 12/1996 |
| WO | WO 98/45453 | 10/1998 |
| WO | WO 99/31990 | 7/1999 |
| WO | WO 00/32758 | 6/2000 |
| WO | WO 01/39602 A1 | 6/2001 |
| WO | WO 02/00852 | 1/2002 |
| WO | WO 02/03805 | 1/2002 |
| WO | WO 02/065854 | 8/2002 |
| WO | WO 02/066622 | 8/2002 |

OTHER PUBLICATIONS

Wolff, A. M., O. C. Hansen, U. Poulsen, S. Madrid, P. Stougaard (2001), Protein Expression and Purification., vol. 22, pp. 189–199. "Optimization of the Production of *Chondrus crispus* Hexose Oxidase in *Pichia pastoris*".

Kerschensteiner, D. D. Diss. Abstr. Int. B 1978, 39(7), 3299, CAN 90: 117113 AN 1978:117113 CAPLUS, "The mechanism of action and the state of copper in hexose oxidase".

U.S. Appl. No. 10/040,394, filed Jan. 9, 2002.

U.S. Appl. No. 10/150,429, filed May 17, 2002.

U.S. Appl. No. 09/932,923, filed Aug. 21, 2001.

U.S. Appl. No. 09/824,053, filed Apr. 3, 2001.

Bean and Hassid, 1956, J. Biol. Chem. , 218: 425–436.

Ikawa, 1982, Methods Enzymol., 89: 145–149.

Sullivan et al., 1973, Biochemica et Biophysica Acta, 309:11–22.

Rand, 1972, Journal of Food Science, 37:698–701.

Bak et al., "A Method for Testing the Strengthening Effect of Oxidative Enzymes in Dough", presented at a symposium entitled "Wheat Structure, Biochemistry and Functionality", Reading UK, Apr. 10–12, 1995.

Christiansen, 1993, "Application of Oxidoreductases for Food Preservation" in Progress Report of R&D Projects and Concerted Actions published by the European Communities, Luxembourg, 1993, p. 32–36.

Kerschensteiner, The Mechanism of Action and the State of Copper in Hexose oxidase, Thesis, 1978, p. iii–xiii.

Perella, F.W., Analytical Biochemistry, 174:437–447 (1988).

AACC Method 36–01 A.

"Enzyme Technology in Flour Milling and Baking", *Baking Industry Europe* (Alan Gordon, editor), S. Haarasilta and T. Pullinen (1993), pp. 49–52.

"Enzyme Nomenclature 1984 (Recommendations of the Nomenclature Committee of the International Union of Biochemistry on the Nomenclature and Classification of Enzyme–Catalysed Reactions)" (1984), pp. v, ix, and 50–51.

"Glucose Oxidase: Production, Properties, Present and Potential Applications", *Soc. Chem. Ind.* (Londen), (1961), L.A. Underkofler, p. 72–86.

"Methods in Enzymology", *Biomass Part B* Glucose Oxidase of *Phanerochaete chrysosporium*, R.L. Kelley and C.A. Reddy (1988), 161, pp. 306–317.

Definition of "hexose", Webster Dictionary, p. 1065.

"Baking Science & Technology", E.J. Pyler (1982), vol. 1, pp. 314–316.

"Novel Enzyme Combinations A New Tool to Improve Baking Results", *Agro–Industry Hi–Tech*. S. Haarasilta and T. Pullinen, (May/Jun. 1992), p. 12–13.

"Enzyme Nomenclature (Recommendations of the Nomenclature Committee of the International Union of Biochemistry and Molecular Biology on the Nomenclature and Classification of Enzymes)" (1992), p. 56.

"Enzyme Function", Experimental Report from Novo Nordisk, Mar. 13, 1997, 2 pages.

*J. Chromatog.*, Knoll et al., 55 (1971), 425–428.

"DEEO®" A glucose oxidase and catalase enzyme system product sheet from Miles laboratories– Enzymes from Miles (technical Information) (1976), 5 pages.

"Enzymes in Food Processing", $2^{nd}$ Ed. by G. Reed, Universal Foods Corporation, Academic Press (1975), p. 222–229.

"Properties and Applications of the Fungal Enzyme Glucose Oxidase", reprinted from "Proceedings of the International Symposium on Enzyme Chemistry", Tokyo and Kyoto, (1957) L.A. Underkofler, (1958), pp. 486–490.

"The Oxidation of Glucose and Related Compounds by Glucose Oxidase from *Aspergillus niger*", *Biochemistry*, Pazur et al., vol. 3(4), 1964, 578–583.

"Technology of Cereals (with special reference to wheat)", $2^{nd}$ Ed., Pergamom Press Ltd. N. L. Kent, (1975), pp. iv–v, 48–49, and 72–73.

"Gluzyme™" product sheet from Novo Nordisk Enzyme Process Division, Jan. 1994, 2 pages.

Derwent Publications Ltd., London, GB; AN 73–30288u XP002012361 & JP, A48016612 (EISAI Co. Ltd).

Clare et al., 1991, Bio/Technology 9:455–460 [3].

Cregg et al., 1987, In: Biological Research on Industrial Yeast, vol. II, Stewart, G.G. et al. (Eds.), pp. 1–18 [4].

Fernandez et al., 1992, Analytical Biochemistry, 201:255–264 [5].

Pedersen et al., 1996, J. Biol. Chem. 271:2514–2522 [10].

Sahm et al., 1973, Eur. J. Biochem. 37:250–256 [12].

Tschopp et al., 1987, Bio/Technology 5:1305–1308 [17].

Barkholt, V. and A.L. Jensen, 1989, Amino Acid Analysis: Determination of Cysteine plus Half–Cysteine in Proteins after Hydrochloric Acid Hydrolysis with a Disulfide Compound as Additive, Analytical Biochemistry, 177:318–322.

Fernandez, J. et al., 1994, An Improved Procedure for Enzymatic Digestion of Polyvinylidene Difluoride–Bound Proteins for Internal Sequence Analysis, Analytical Biochemistry, 218:112–117.

Groppe, J.C. and Morse, D.E., 1993, Isolation of full–length RNA templates for reverse transcription from tissues rich in RNase and proteoglycans, Anal. Biochem., 210:337–343.

Kerschensteiner, D.A. and Klippenstein, D.A., 1978, Purification Mechanism and State of Copper in Hexose Oxidase, Federation Proceedings 37:1816 abstract.

Laemmli, U.K., 1970, Cleavage of structural Proteins during the Assembly of the Head of Bacteriophage T4, Nature (London), 227:680–685.

Schägger, H. and von Jagow, G., 1987, Tricine–Sodium Dodecyl Sulfate–Polyacrylamide Gel Electrophoresis for the Separation of Proteins in the Range from 1 to 100 kDa, Analytical Biochemistry 166:368–379.

Sock, Jr. and Rohringer, R., 1988, Activity Staining of Blotted Enzymes by Reaction Coupling with Transfer Membrane–Immobilized Auxiliary Enzymes, Analytical Biochemistry 171:310–319.

Yeh, K–W, Juang, R.H and Su, J–C, A Rapid and efficient method for RNA isolation from plants with high–carbohydrate content, Focus 13 (3):102–103, 1991.

Maes et al., Analytica Chimica Acta, 284 (1993) 281–290.

Sambrook, J., Fritsch, E.F. and Maniatis, T., 1989, Molecular Cloning, A Laboratory Manual $2^{nd}$ Ed. Cold Spring Harbor Laboratory Press, Cold Spring Harbor, NY.

Dowling et al., "Hexose Oxidation by an enzyme system of Malleomyces Pseudomallei", Journal of Bacteriology (1956) 72:555–560.

Bean et al., "Carbohydrate Metabolism of Citrus Fruits", Journal of Biological Chemistry (1961) 236: 1235–1240.

Witteveen, C.F.B.: Thesis "Gluconate formation and polyol metabolism in *Aspergillus niger*", selected pages (1993).

AACC Method 54–10.

Ellman, George L.: "A Colorimetric Method for Determining Low Concentrations of Mercaptans", Archives of Biochemistry and Biophysics (1958) 74: 443–450.

Poulsen, C., et al., "Purification and Characterization of a Hexose Oxidase with Excellent Strengthening Effects in Bread", *Cereal Chem.*, 75(1):51–57 (1998).

"Effect of Different Hexose Oxidase and Other Oxide Reductases in Dough", Experimental Data Submitted by Applicants in European Counterpart Application 96917368.

Krog, N.J., "Dynamic and Unique Monoglycerides", *Cereal Foods World*, 24(1): 10–11 (1979).

Matos, A.R., et al., "A Novel Patatin–like Gene Stimulated by Drought Stress Encodes a Galactolipid Acyl Hydrolase", *FEBS Letters*, 491: 188–192 (2001).

Withers–Martinez, C., et al., "A Pancreatic Lipase with a Phospholipase A1 activity: Crystal Structure of a Chimerica Pancreatic Lipase–Related Protein 2 from Guinea Pig", *Structure* 4(11): 1363–1374 (1996).

Cordle, R.A., "The Hydrophobic Surface of Colipase Influences Lipase Activity at an Oil–Water Interface", *Journal of Lipid Research*, 39: 1759–1767 (1998).

Sahsah, Y., et al., "Purification and Characterization of a Soluble Lipolytic Acylhydrolase from Cowpea (*Vigna unguiculata* L.) Leaves", *Biochemica et Biophysica Acta*, 1215: 66–73 (1994).

O'Sullivan, J., et al., "A Galactolipase Activity Associated with the Thylakoids of Wheat Leaves (*Triticum aestivum* L.)", *J. Plant Physiol.*, 131:393–404 (1987).

Carriere, F., et al., "Pancreatic Lipase Structure–Function Relationships by Domain Exchange," *Biochemistry*, 36: 239–248 (1997).

Bornscheuer, U.T., "Lipase–Catalyzed Syntheses of Monoacylglycerols", *Enzyme and Microbial Technology*, 17: 578–586 (1995).

Hou, C.T., "pH Dependence and Thermostability of Lipases from Cultures from the ARS Culture Collection", *Journal of Industrial Microbiology*, 13:242–248 (1994).

Villeneuve, P., et al., "Lipase Specificities: Potential Application in Lipid Bioconversions", *Inform*, 8(6): 640–650 (1997).

Cammann, K., et al., "Chemical Sensors and Biosensors–Principles and Applications", *Angew. Chem. Int. Ed. Engl.*, 30: 516–539 (1991).

Allen, R.M. et al., "Low–Level Electrochemical Detection of Glucose Oxidase and a Glucose Oxidase Conjugate", *Biosensors and Bioelectronics*, 10:621–631 (1995).

Wiseman, A., "Immobilization of Glucose Oxidase into Membranes as Sensors for Food Analysis", *Elsevier Science Publishers*, (1987).

Wilson, R., et al., "Glucose Oxidase: An Ideal Enzyme", *Biosensors and Bioelectronics*, 7:165–185 (1992).

Raba, J., et al., "Glucose Oxidase as an Analytical Reagent", *Critical Reviews in Analytical Chemistry*, 25(1):1–42 (1995).

Volc, J., et al., "Glucose–2 Oxidase Activity in Mycelial Cultures of Basidiomycetes", *Folia Microbiol.*, 30:141–147 (1985).

Giffhorn, F., "Fungal Pyranose Oxidases: Occurrence, Properties and Biotechnical Applications in Carbohydrate Chemistry", *Appl. Microbiol. Biotechnol.*, 54:727–740 (2000).

Certificate of Analysis for Maltose Monohydrate, SIGMA.

Lin, Shuen–Fuh et al., "Purification and Characterization of a Novel Glucooligosaccharide Oxidase from *Acremonium strictum* T1", *Biochimica et Biophysica Acta*, 1118:41–47 (1991).

Pazur, J.H., et al., "Comparison of the action of Glucoamylase and Glucosyltransferase on D–Glucose, Maltose, and Malto–Oligosaccharaides," *Carbohydrate Research*, 58:193–202 (1977).

Qi Si, J., "New Enzymes for the Baking Industry", *Food Tech Europe*, 3(I):60–64 (1996), Novo Nordisk Ferment Ltd.

Weipert, D., "Rheologie von Roggenteigen., II. Der Einfluss der Enzyme unterschiedlicher Spezifität auf dzas rheologische Verhalten des Teiges", *Getreide, Mehl Und Brot*, 26(10):275–280 (1972); and English language translation of Abstract.

Nicolas, J., "Mise au Point sur l'action d'enzymers d'oxydoréduction en technologie boulangère. La maturation des farines de blétendre et le pétrissage des pâtes", *Ann. Technol. Agric.*, 28(4):445–468 (1979); and English language translation of Abstract.

Mine, Y., "Application of the Enzymatic Methods to the Determination of Contaminated Yolk in Egg White", *Food Research International*, 29(1):81084 (1996).

Pub. No. 06–296467 (JP 6296467), Oct. 25, 1994, Section No. FFFFFF, vol. 94, No. 10, p. FFFFFF, FF, FFFF (FFFFFFFF) believed to be Patent Abstracts of Japan vol. 095, No. 001.

Patent Abstracts of Japan Vo. 016, No. 528 (C–1001).

Marion Didier, et al., "Lipids, Lipid–Protein Interactions and the Quality of Baked Cereal Products," *Interactions: The Keys to Cereal Quality*, (ed. Hamer & Hoseney), Chapter 6, pp. 131–167 (1998).

Conference May 6–8, 1999 in Santorini, Greece, "Lipases of Lipids Structure, Function and Biotechnological Applications," Slides presented by Charlotte Poulsen.

C.H. Poulsen, et al., "Effect and Functionality of Lipases in Dough and Bread," *The First European Symposium on Enzymes and Grain Processing*, pp. 204–214 (1997).

D. Marion, et al., "Wheat Lipids and Lipid–Binding Proteins: Structure and Function," *Wheat Structure Biochemistry and Functionality*, ed. Scholfield JP), pp 245–260 (1995).

"Unique Chance for Better Bread," *Direct, A Newsletter from Danisco Ingredients*, (1996).

Haarasilta, S., T. Pullinen (1993) in Baking Industry Europe (Alan Gordon, editor), pp. 49–52.

Sullivan, James Denis Jr., Diss. Abstr. Int. B, 1973, 34(5), 1875, Can 80: 105204 AN 1974: 105204 Caplus, "Purification and characterization of hexose oxidase from the red alga Chondrus crispus".

Groen, B. W., s De Vries, J. A. Duine (1997), Eu. J. Biochem., vol. 244, pp. 858–861, "Characterization of hexose from the red seaweed Chondrus crispus".

Wolff, A. M., O. C. Hansen U. Poulsen, S. Madrid, P. Stougaard (2001), Protein Expression and Purification., vol. 22, pp. 189–199. "Optimization of the Production of Chondrus crispus Hexose Oxidase in Pichia pastoris".

Kerschensteiner, D. D. Diss. Abstr. Int. B 1978, 39(7), 3299, Can 90:117113 An 1978:117113 Caplus, "The mechanism of action and the state of cooper in hexose oxidase".

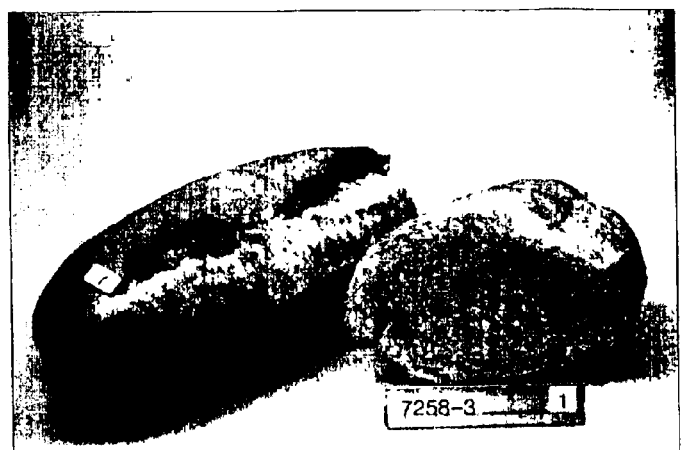
Figure 1: 7.5 ppm Lipopan F and 60 ppm TS-E 680
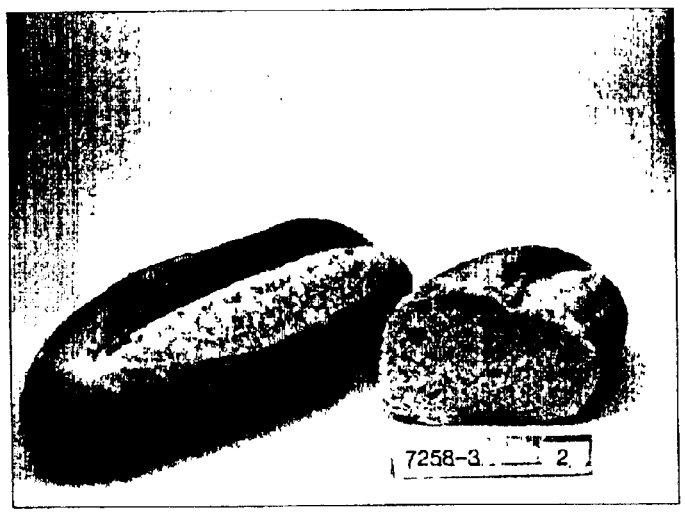
Figure 2: 40 ppm Lipopan F
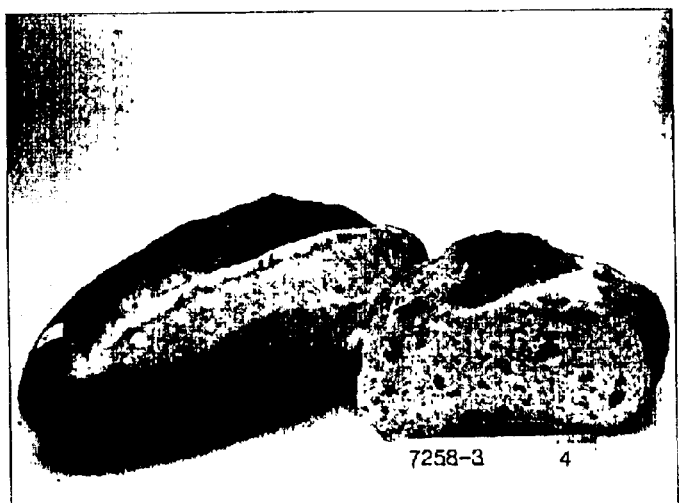
Figure 3: 100 ppm TS-E 861

METHOD OF IMPROVING THE PROPERTIES OF A FLOUR DOUGH, A FLOUR DOUGH IMPROVING COMPOSITION AND IMPROVED FOOD PRODUCTS

CROSS-REFERENCE TO RELATED APPLICATIONS

This application claims the benefit of priority of the filing date of U.S. Provisional Patent Application No. 60/398,020, filed Jul. 24, 2002. This application is also a continuation-in-part of U.S. patent application Ser. No. 09/932,923, filed Aug. 21, 2001, now U.S. Pat. No. 6,726,942, which is a continuation of application Ser. No. 08/676,186 filed Sep. 12, 1996, now U.S. Pat. No. 6,358,543, which was a continuation-in-part of application Ser. No. 08/483,870, filed Jun. 7, 1995, abandoned. The Ser. No. 08/483,870 application was a U.S. national phase of PCT/DK96/00239, filed Jun. 4, 1996. This application is additionally a continuation-in-part of application Ser. No. 10/040,394, filed Jan. 9, 2002, which was a divisional of application Ser. No. 09/402,664, filed Oct. 22, 1999, now U.S. Pat. No. 6,406,723. U.S. Pat. No. 6,406,723 was the U.S. national phase of PCT/DK98/00136, filed Apr. 3, 1998, which claimed priority from DK0400/97, filed Apr. 9, 1997. This application is also a continuation-in-part of U.S. application Ser. No. 10/150,429, filed May 17, 2002, which claims priority from UK Application 0112226.6, filed May 18, 2001, and U.S. Application No. 60/347,007, filed Jan. 9, 2002. We claim the benefit of priority dates of all the above applications. This application also claims the benefit of priority of the filing date of Great Britain Application 0211975.8, filed May 24, 2002. The contents of all of the above applications are incorporated herein by reference to the extent they are consistent with this application and inventions described herein.

FIELD OF INVENTION

The invention pertains to the provision of flour doughs having improved rheological properties and farinaceous food products having improved quality characteristics and it provides a maltose oxidizing oxidoreductase-containing compo-sition capable of conferring such improved properties on doughs and finished food products made herefrom when it is added as a component to the doughs, and a method of preparing improved doughs and farinaceous food products.

More in particular, the present invention relates to the field of food manufacturing, in particular to the preparation of improved bakery products and other farinaceous food products. Specifically, the invention concerns the use of a new combination for improving the stability and/or machineability of dough and/or improving the quality of baked and dried products made from such doughs.

In a preferred aspect, the present invention relates to:
a method of improving the rheological and/or machine-ability properties of a flour dough and/or the quality of the product made from the dough, comprising adding to the dough a combination comprising a Hox and an emulsifying agent.

Teachings relating to this preferred aspect now follow.

TECHNICAL BACKGROUND AND PRIOR ART

The invention relates in particular to a method of providing flour doughs having improved rheological properties and to finished baked or dried products made from such doughs, which have improved textural, eating quality and dimensional characteristics.

In this connection, the "strength" or "weakness" of doughs is an important aspect of making farinaceous finished products from doughs, including baking. The "strength" or "weakness" of a dough is primarily determined by its content of protein and in particular the content and the quality of the gluten protein is an important factor in that respect. Flours with a low protein content are generally characterized as "weak". Thus, the cohesive, extensible, rubbery mass which is formed by mixing water and weak flour will usually be highly extensible when subjected to stress, but it will not return to its original dimensions when the stress is removed.

Flours with a high protein content are generally characterized as "strong" flours and the mass formed by mixing such a flour and water will be less extensible than the mass formed from a weak flour, and stress which is applied during mixing will be restored without breakdown to a greater extent than is the case with a dough mass formed from a weak flour.

Strong flour is generally preferred in most baking contexts because of the superior rheological and handling properties of the dough and the superior form and texture qualities of the finished baked or dried products made from the strong flour dough.

Dough quality may be largely dependent on the type or types of flour present in the dough and/or the age of the flour or flours.

Doughs made from strong flours are generally more stable. Stability of a dough is one of the most important characteristics of flour doughs. According to American Association of Cereal Chemists (AACC) Method 36-01A the term "stability" can be defined as "the range of dough time over which a positive response is obtained and that property of a rounded dough by which it resists flattening under its own weight over a course of time". According to the same method, the term "response" is defined as "the reaction of dough to a known and specific stimulus, substance or set of conditions, usually determined by baking it in comparison with a control"

Within the bakery and milling industries it is known to use dough "conditioners" to strengthen the dough to increase its stability and strength. Such dough conditioners are normally non-specific oxidizing agents such as eg iodates, peroxides, ascorbic acid, K-bromate or azodi-carbonamide and they are added to dough with the aims of improving the baking performance of flour to achieve a dough with improved stretchability and thus having a desirable strength and stability. The mechanism behind this effect of oxidizing agents is that the flour proteins, in particular gluten contains thiol groups which, when they become oxidized, form disulphide bonds whereby the protein forms a more stable matrix resulting in a better dough quality and improvements of the volume and crumb structure of the baked products.

In addition to the above usefulness of ascorbic acid/ascorbate as a dough conditioner due to its oxidizing capacity, these compounds may also act as substrate for an oxidoreductase, ascorbate oxidase which is disclosed in EP 0 682 116 Al. In the presence of its substrate, this enzyme converts ascorbic acid/ascorbate to dehydroascorbic acid and $H_2O_2$. This prior art does not suggest that ascorbic acid oxidase in the presence of ascorbic acid/ascorbate might have a dough conditioning effect, but assumingly this is the case.

However, the use of several of the currently available oxidizing agents is either objected to by consumers or is not permitted by regulatory bodies and accordingly, it has been attempted to find alternatives to these conventional flour and dough additives and the prior art has i.a. suggested the use of glucose oxidase for this purpose. In addition, the prior art has inter alia (i.a.) suggested the use of oxidoreductases such as carbohydrate oxidase, glycerol oxidase and hexose oxidase for this purpose.

Thus, U.S. Pat. No. 2,783,150 discloses the addition of glucose oxidase to flour to improve dough strength and texture and appearance of baked bread.

CA 2,012,723 discloses bread improving compositions comprising cellulolytic enzymes such as xylanases and glucose oxidase, the latter enzyme being added to reduce certain disadvantageous effects of the cellulolytic enzymes (reduced dough strength and stickiness) and it is disclosed that addition of glucose to the dough is required to obtain a sufficient glucose oxidase activity.

JP-A-92-084848 suggests the use of a bread improving composition comprising glucose oxidase and lipase.

EP-Bl-321 811 discloses the use of an enzyme composition comprising sulfhydryl oxidase and glucose oxidase to improve the rheological characteristics of doughs. It is mentioned in this prior art document that the use of glucose oxidase alone has not been successful.

In EP-B1-338 452 is disclosed an enzyme composition for improving dough stability, comprising a mixture of cellulase/hemicellulase, glucose oxidase and optionally sulfhydryl oxidase.

However, the use of glucose oxidase as a dough improving additive has the limitation that this enzyme requires the presence of sufficient amounts of glucose as substrate in order to be effective in a dough system and generally, the glucose content in cereal flours is low. Therefore, the absence of glucose in doughs or the low content hereof in doughs will be a limiting factor for the effectiveness of glucose oxidase as a dough improving agent.

In contrast hereto, the content of maltose in cereal flours is generally significantly higher than that of glucose and accordingly, a freshly prepared dough will normally contain more maltose than glucose. Thus, in an experiment where the content of sugars in supernatants from suspensions of wheat flour and a dough prepared from the flour and further comprising water, yeast, salt and sucrose (as described in the following example 2.3) were analyzed, the following values (% by weight calculated on flour) were found:

|  | Flour | Dough |
| --- | --- | --- |
| Sucrose | 0.3 | <0.01 |
| Galactose | 0.001 | 0.01 |
| Glucose | 0.25 | 0.72 |
| Maltose | 2.6 | 1.4 |
| Fructose | 0.08 | 0.67 |
| Lactose | <0.01 | <0.01 |

In addition, the content of maltose remains at a relatively high level in a dough which is leavened by yeast, since the yeast primarily utilizes glucose, or it may even increase in the dough e.g. during proofing due to the activity of starch degrading enzymes such as e.g. β-amylase, which is inherently present in the flour or is added to the dough.

Whereas the prior art has recognized the useful improving effects of glucose oxidase on the rheological characteristics of bread doughs and on the quality of the corresponding baked products, it has also been realized that the use of this enzyme has several drawbacks. Thus, it may be required to add sucrose or glucose as substrate to the dough to obtain a sufficient effect and glucose oxidase does not constantly provide a desired dough or bread improving effect when used alone without the addition of other enzymes.

However, it has now been found that the addition of an oxidoreductase, which is capable of oxidizing maltose, including hexose oxidase as a sole dough conditioning agent, i.e. without concomitant addition of substrate for the added enzyme, or of other enzymes, to a farinaceous dough results in an increased resistance hereof to breaking when the dough is stretched, i.e. this enzyme confers in itself to the dough an increased strength whereby the dough becomes less prone to mechanical deformation. It is contemplated that this effect of addition of hexose oxidase to a dough is the result of the formation of cross-links between thiol groups in sulphur-containing amino acids in wheat gluten which occurs when the $H_2O_2$ generated by the enzyme in the dough reacts with the thiol groups which are hereby oxidized.

Hexose oxidase (D-hexose: $O_2$-oxidoreductase, EC 1.1.3.5) is an enzyme which in the presence of oxygen is capable of oxidizing D-glucose and several other reducing sugars including maltose, glucose, lactose, galactose, xylose, arabinose and cellobiose to their corresponding lactones with subsequent hydrolysis to the respective aldobionic acids. Accordingly, hexose oxidases differ from glucose oxidase which can only convert D-glucose, in that hexose oxidases can utilize a broader range of sugar substrates. The oxidation catalyzed by the enzyme can be illustrated as follows:

D-Glucose+$O_2$->δ-D-gluconolactone+$H_2O_2$, or

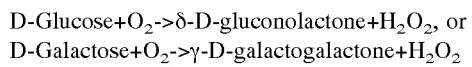

Hexose oxidase (in the following also referred to as HOX) has been isolated from several red algal species such as *Iridophycus flaccidum* (Bean and Hassid, 1956, J. Biol. Chem., 218:425–436) and *Chondrus crispus* (Ikawa 1982, Methods Enzymol., 89:145–149). Additionally, the algal species *Euthora cristata* (Sullivan et al. 1973, Biochemica et Biophysica Acta, 309:11–22) has been shown to produce HOX.

Other potential sources of hexose oxidase according to the invention include microbial species or land-growing plant species. Thus, as an example of such a plant source, Bean et al., Journal of Biological Chemistry (1961) 236: 1235–1240, have disclosed an oxidoreductase from citrus fruits which is capable of oxidizing a broad range of sugars including D-glucose, D-galactose, cellobiose, lactose, maltose, D-2-deoxyglucose, D-mannose, D-glucosamine and D-xylose. Another example of an enzyme having hexose oxidase activity is the enzyme system of *Malleomyces mallei* disclosed by Dowling et al., Journal of Bacteriology (1956) 72:555–560.

It has been reported that hexose oxidase isolated from the above natural sources may be of potential use in the manufacturing of certain food products. Thus, hexose oxidase isolated from *Iridophycus flaccidum* has been shown to be capable of converting lactose in milk with the production of the corresponding aldobionic acid and has been shown to be of potential interest as an acidifying agent in milk, e.g. to replace acidifying microbial cultures for that purpose (Rand, 1972, Journal of Food Science, 37:698–701). In that respect, hexose oxidase has been mentioned as a more interesting enzyme than glucose oxidase, since this latter enzyme can only be enzymatically effective in milk or other food products not containing glucose or having a low content of glucose, if glucose or the lactose-degrading enzyme lactase which convert the lactose to glucose and galactose, is also added.

The capability of oxidoreductases including that of hexose oxidase to generate hydrogen peroxide has also been utilized to improve the storage stability of certain food products including cheese, butter and fruit juice as it is disclosed in JP-B-73/016612. It has also been suggested that oxidoreductases may be potentially useful as antioxidants in food products.

However, the present invention has demonstrated that hexose oxidase is highly useful as a dough conditioning agent in the manufacturing of flour dough products including not only bread products but also other products made from flour doughs such as noodles and alimentary paste products.

WO 94/04035 discloses a method of improving properties of a dough (with and without fat) and/or baked product made from dough by adding a lipase of microbial origin to the dough. The use of the microbial lipase resulted in an increased volume and improved softness of the baked product. Furthermore an antistaling effect was found.

EP 1 108 360 A1 discloses a method of preparing a flour dough. The method comprises adding to the dough components an enzyme that under dough conditions is capable of hydrolysing a nonpolar lipid, a glycolipid and a phospholipid, or a composition containing said enzyme and mixing the dough components to obtain the dough.

WO 02/03805 discloses that the addition to dough of a combination of two lipases with different substrate specificities. The combination produces a synergistic effect on the dough or on a baked product made from the dough. Optionally, an additional enzyme may be used together with the lipase.

SUMMARY OF THE INVENTION

Accordingly, the invention relates in a first aspect to a method of improving the rheological properties of a flour dough and the quality of the finished product made from the dough, comprising adding to the dough ingredients, dough additives or the dough an effective amount of an oxidoreductase which at least is capable of oxidizing maltose, such as e.g. a hexose oxidase.

In a further aspect, there is also provided a dough bakery product improving composition comprising an oxidoreductase which at least is capable of oxidizing maltose, and at least one further dough ingredient or dough additive.

In still further aspects, the invention pertains to a method of preparing a bakery product, comprising preparing a flour dough including adding an effective amount of an oxidoreductase which at least is capable of oxidizing maltose and baking the dough, and a method of preparing a dough-based food product comprising adding to the dough an effective amount of a maltose oxidizing oxidoreductase.

In addition, we have surprisingly found that a combination of a Hox and an emulsifying agent results in particularly advantageous properties in dough and dough products and/or in baked products therefrom. In particular the stability (e.g. shock stability) and/or rheological (e.g. decrease in stickiness) and/or machineability properties and/or the resultant volume of either the dough and/or baked products (e.g. baked products with better crumb structure and/or homogeneity) is/are improved. Furthermore, the combination of the Hox and emulsifying agent results in an improvement in bread quality, in particular in respect of specific volume and/or crumb homogeneity, which is not a simple additive effect, but may reflect a synergistic effect of these types of enzymes.

The invention further relates to the use of a Hox and an emulsifying agent to improve the rheological and/or machineability properties of dough.

The invention further relates to the use of a Hox and an emulsifying agent to improve the volume of a baked product made from a dough.

DETAILED DISCLOSURE OF THE INVENTION

In one aspect, the present method contemplates a method of improving the rheological properties of flour doughs. The method comprises, as it is mentioned above, the addition of an effective amount of a maltose oxidizing oxidoreductase either to a component of the dough recipe or to the dough resulting from mixing all of the components for the dough. In the present context, "an effective amount" is used to indicate that the amount is sufficient to confer to the dough and/or the finished product improved characteristics as defined herein.

In another aspect the invention provides a method of improving the rheological and/or machineability properties of a flour dough and/or the quality (e.g. volume) of the product made from the dough, comprising adding to the dough a combination comprising a Hox and an emulsifying agent.

Factors which influence the rheological properties and/or the machineability include stickiness and extensibility.

In another aspect the invention provides a method of improving the rheological and/or machineability properties of a flour dough and/or the quality (e.g. volume) of the product made from the dough, comprising adding to the dough a combination comprising a Hox and an emulsifying agent wherein the flour dough comprises at least one further dough additive or ingredient.

In another aspect the invention provides a method of improving the rheological and/or machineability properties of a flour dough and/or the quality (e.g. volume) of the product made from the dough, comprising adding to the dough a combination comprising a Hox and an emulsifying agent wherein the product is selected from the group consisting of a bread product, a noodle product, a cake product, a pasta product and an alimentary paste product.

In another aspect the invention provides a method of improving the rheological and/or machineability properties of a flour dough and/or the quality (e.g. volume) of the product made from the dough, comprising adding to the dough a combination comprising a Hox and an emulsifying agent wherein at least one further enzyme is added to the dough ingredients, dough additives or the dough.

In another aspect the invention provides a dough improving composition comprising a Hox and an emulsifying agent.

In another aspect the invention provides a dough improving composition comprising a Hox and an emulsifying agent wherein the flour dough comprises at least one further dough additive or ingredient.

In another aspect the invention provides use of a dough improving composition comprising a Hox and an emulsifying agent in the manufacture of a product made from dough wherein the product is selected from the group consisting of a bread product, a noodle product, a cake product, a pasta product and an alimentary paste product.

In another aspect the invention provides a dough improving composition comprising a Hox and an emulsifying agent wherein at least one further enzyme is added to the dough ingredients, dough additives or the dough.

In another aspect the invention provides use of a dough improving composition comprising a Hox and an emulsifying agent wherein said composition improves the rheological and/or machineability properties of flour dough.

In another aspect the invention provides use of a dough improving composition comprising a Hox and an emulsifying agent wherein said composition improves the volume of a baked product made from a flour dough.

In another aspect the invention provides a dough for addition to a sponge wherein said dough comprises a Hox and an emulsifying agent.

In another aspect the invention provides a dough for addition to a sponge wherein said dough comprises a Hox and an emulsifying agent and wherein the dough comprises at least one further dough additive or ingredient.

Hexose Oxidase

In one useful embodiment of the method according to the invention, the oxidoreductase is a hexose oxidase.

The term "Hox" as used herein refers to Hexose oxidase (D-hexose:$O_2$-oxidoreductase, EC 1.1.3.5). Below discloses some of the sources of Hox. WO 96/40935 discloses a method of producing Hox by recombinant DNA technology. U.S. Pat. No. 6,251,626 discloses hexose oxidase sequences.

The Hox may be isolated and/or purified from natural sources or it may be prepared by use of recombinant DNA techniques.

The Hox may be a variant or derivative of a natural Hox.

The Hox, or the variant or derivative of a natural Hox, is capable of oxidising maltose in the dough.

Preferably the Hox is added in a substantially pure and/or substantially isolated form.

Hexose oxidase can, as it is described in details herein, be isolated from marine algal species naturally producing that enzyme. Such species are found in the family Gigartinaceae which belong to the order Gigartinales. Examples of hexose oxidase producing algal species belonging to Gigartinaceae are *Chondrus crispus* and *Iridophycus flaccidum*. Also algal species of the order Cryptomeniales including the species *Euthora cristata* are potential sources of hexose oxidase.

When using such natural sources for hexose oxidase, the enzyme is typically isolated from the algal starting material by extraction using an aqueous extraction medium. As starting material may be used algae in their fresh state as harvested from the marine area where they grow, or the algal material can be used for extraction of hexose oxidase after drying the fronds e.g. by air-drying at ambient temperatures or by any appropriate industrial drying method such as drying in circulated heated air or by freeze-drying. In order to facilitate the subsequent extraction step, the fresh or dried starting material may advantageously be comminuted e.g. by grinding or blending.

As the aqueous extraction medium, buffer solutions e.g. having a pH in the range of 5–8, such as 0.1 M sodium phosphate buffer, 20 mM triethanolamine buffer or 20 mM Tris-HCl buffer are suitable. The hexose oxidase is typically extracted from the algal material by suspending the starting material in the buffer and keeping the suspension at a temperature in the range of 0–20° C. such as at about 5° C. for 1 to 5 days, preferably under agitation.

The suspended algal material is then separated from the aqueous medium by an appropriate separation method such as filtration, sieving or centrifugation and the hexose oxidase is subsequently recovered from the filtrate or supernatant. Optionally, the separated algal material is subjected to one or more further extraction steps.

Since several marine algae contain coloured pigments such as phycocyanins, it may be required to subject the filtrate or supernatant to a further purification step whereby these pigments are removed. As an example, the pigments may be removed by treating the filtrate or supernatant with an organic solvent in which the pigments are soluble and subsequently separating the solvent containing the dissolved pigments from the aqueous medium. Alternatively, pigments may be removed by subjecting the filtrate or supernatant to a hydrophobic interaction chromatography step.

The recovery of hexose oxidase from the aqueous extraction medium is carried out by any suitable conventional methods allowing isolation of proteins from aqueous media. Such methods, examples of which will be described in details in the following, include conventional methods for isolation of proteins such as ion exchange chromatography, optionally followed by a concentration step such as ultrafiltration. It is also possible to recover the enzyme by adding substances such as e.g. $(NH_4)_2SO_4$ or polyethylene glycol (PEG) which causes the protein to precipitate, followed by separating the precipitate and optionally subjecting it to conditions allowing the protein to dissolve.

For certain applications of hexose oxidase it is desirable to provide the enzyme in a substantially pure form e.g. as a preparation essentially without other proteins or non-protein contaminants and accordingly, the relatively crude enzyme preparation resulting from the above extraction and isolation steps may be subjected to further purification steps such as further chromatography steps, gel filtration or chromatofocusing as it will also be described by way of example in the following.

Further Dough Additives or Ingredients (Components)

In a preferred embodiment of the method according to the invention, a flour dough is prepared by mixing flour with water, a leavening agent such as yeast or a conventional chemical leavening agent, and an effective amount of hexose oxidase under dough forming conditions. It is, however, within the scope of the invention that further components can be added to the dough mixture.

Typically, such further dough components include conventionally used dough components such as salt (such as sodium chloride, calcium acetate, sodium sulfate or calcium sulfate), sweetening agents such as sugars, syrups or artificial sweetening agents, lipid substances including shortening, margarine, butter or an animal or vegetable oil, glycerol and one or more dough additives such as emulsifying agents, starch degrading enzymes, cellulose or hemicellulose degrading enzymes, proteases, lipases, non-specific oxidizing agents such as those mentioned above, flavouring agents, lactic acid bacterial cultures, vitamins, minerals, hydrocolloids such as alginates, carrageenans, pectins, vegetable gums including e.g. guar gum and locust bean gum, and dietary fiber substances.

The dough may also comprise other conventional dough ingredients, e.g.: proteins, such as milk powder, gluten, and soy; eggs (either whole eggs, egg yolks or egg white); an oxidant such as ascorbic acid, potassium bromate, potassium iodate, azodicarbonamide (ADA) or ammonium persulfate; an amino acid such as L-cysteine; a sugar.

The dough may comprise fat such as granulated fat or shortening.

The further dough additive or ingredient can be added together with any dough ingredient including the flour, water or optional other ingredients or additives, or the dough improving composition. The further dough additive or ingredient can be added before the flour, water, optional other ingredients and additives or the dough improving composition. The further dough additive or ingredient can be added after the flour, water, optional other ingredients and additives or the dough improving composition.

The further dough additive or ingredient may conveniently be a liquid preparation. However, the further dough additive or ingredient may be conveniently in the form of a dry composition.

Preferably the further dough additive or ingredient is selected from the group consisting of a vegetable oil, a vegetable fat, an animal fat, shortening, glycerol, margarine, butter, butterfat and milk fat.

Preferably the further dough additive or ingredient is at least 1% the weight of the flour component of dough. More preferably, the further dough additive or ingredient is at least 2%, preferably at least 3%, preferably at least 4%, preferably at least 5%, preferably at least 6%.

If the additive is a fat, then typically the fat may be present in an amount of from 1 to 5%, typically 1 to 3%, more typically about 2%.

Further Enzymes

In one advantageous embodiment of the above method at least one further enzyme is added to the dough. Suitable examples hereof include a cellulase, a hemicellulase, a xylanase, a starch degrading enzyme, a glucose oxidase, a lipase, a lipoxygenase, an oxidoreductase and a protease.

Among starch degrading enzymes, amylases are particularly useful as dough improving additives. Other useful starch degrading enzymes which may be added to a dough composition include glucoamylases and pullulanases.

The term "xylanase" as used herein refers to xylanases (EC 3.2.1.32) which hydrolyse xylosidic linkages.

The further enzyme can be added together with any dough ingredient including the flour, water or optional other ingredients or additives, or the dough improving composition. The further enzyme can be added before the flour, water, and optionally other ingredients and additives or the dough improving composition. The further enzyme can be added after the flour, water, and optionally other ingredients and additives or the dough improving composition.

The further enzyme may conveniently be a liquid preparation. However, the composition may be conveniently in the form of a dry composition.

In some aspects of the present invention it may be found that some enzymes of the dough improving composition of the invention are capable of interacting with each other under the dough conditions to an extent where the effect on improvement of the rheological and/or machineability properties of a flour dough and/or the quality of the product made from dough by the enzymes is not only additive, but the effect is synergistic.

In relation to improvement of the product made from dough (finished product), it may be found that the combination results in a substantial synergistic effect in respect to crumb homogeneity as defined herein. Also, with respect to the specific volume of baked product a synergistic effect may be found.

Emulsifying Agent

The dough may further comprise a further emulsifier such as mono- or diglycerides, sugar esters of fatty acids, polyglycerol esters of fatty acids, lactic acid esters of monoglycerides, acetic acid esters of monoglycerides, polyoxethylene stearates, or lysolecithin. Among starch degrading enzymes, amylases are particularly useful as dough improving additives. α-amylase breaks down starch into dextrins which are further broken down by β-amylase into maltose. Other useful starch degrading enzymes which may be added to a dough composition include glucoamylases and pullulanases. In the present context, further interesting enzymes are xylanases and other oxidoreductases such as glucose oxidase, pyranose oxidase and sulfhydryl oxidase.

Conventional emulsifiers used in making flour dough products include as examples monoglycerides, diacetyl tartaric acid esters of mono- and diglycerides of fatty acids, and lecithins e.g. obtained from soya.

The emulsifying agent may be an emulsifier per se or an agent that generates an emulsifier in situ.

Examples of emulsifying agents that can generate an emulsifier in situ include enzymes.

Preferably the emulsifying agent is a lipase.

Lipase

The term "lipase" as used herein refers to enzymes which are capable of hydrolysing carboxylic ester bonds to release carboxylate (EC 3.1.1). Examples of lipases include but are not limited to triacylglycerol lipase (EC 3.1.1.3), galactolipase (EC 3.1.1.26), phospholipase (EC 3.1.1.32).

The lipase may be isolated and/or purified from natural sources or it may be prepared by use of recombinant DNA techniques.

Preferably the lipase is selected from the group comprising triacylglycerol lipase, a galactolipase, phospholipase.

More preferably the lipase(s) may be one or more of: triacylglycerol lipase (EC 3.1.1.3), phospholipase A2 (EC 3.1.1.4), galactolipase (EC 3.1.1.26), phospholipase A1 (EC 3.1.1.32), lipoprotein lipase A2 (EC 3.1.1.34).

The lipase may be a variant or derivative of a natural lipase.

For some aspects, preferably the lipase is a phospholipase (including a variant phospholipase).

Preferably the lipase is added in a substantially pure and/or substantially isolated form.

Lipases that are useful in the present invention can be derived from a bacterial species, a fungal species, a yeast species, an animal cell and a plant cell. Whereas the enzyme may be provided by cultivating cultures of such source organisms naturally producing lipase, it may be more convenient and cost-effective to produce it by means of genetically modified cells such as it is described WO 9800136. The term "derived" may imply that a gene coding for the lipase is isolated from a source organism and inserted into a host cell capable of expressing the gene.

WO 02/03805 teaches some of the sources of lipases. The lipases that are taught therein are incorporated herein by reference.

For some aspects of the present invention the lipase may be Lipopan F (supplied by Novozymes) or a variant thereof.

Dough Preparation

The dough is prepared by admixing flour, water, the oxidoreductase according to the invention or the dough improving composition and optionally other possible ingredients and additives. The oxidoreductase or dough improving composition can be added together with any dough ingredient including the flour, the water or dough ingredient mixture or with any additive or additive mixture. The dough improving composition can be added before the flour or water or optional other ingredients and additives. The dough improving composition can be added after the flour or water, or optional other ingredients and additives. The dough can be prepared by any conventional dough preparation method common in the baking industry or in any other industry making flour dough based products.

The dough of the invention generally comprises wheat meal or wheat flour and/or other types of meal, flour or starch such as corn flour, corn starch, maize flour, rice flour, rye meal, rye flour, oat flour, oat meal, soy flour, sorghum meal, sorghum flour, potato meal, potato flour or potato starch.

A preferred flour is wheat flour, but doughs comprising flour derived from other cereal species such as from rice, maize, corn, oat, barley, rye, durra, soy, sorghum and potato are also contemplated.

Preferably the flour dough comprises a hard flour.

The term "hard flour" as used herein refers to flour which has a higher protein content such as gluten than other flours and is suitable for the production of, for example, bread. The term "hard flour" as used herein is synonymous with the term "strong flour".

Preferably the flour dough comprises a hard wheat flour.

The invention also provides a pre-mix comprising flour together with the combination as described herein. The pre-mix may contain other dough-improving and/or bread-improving additives, e.g. any of the additives, including enzymes, mentioned herein.

The dough of the invention may be fresh, frozen, or part-baked.

The dough of the invention can be a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The oxidoreductase or the dough improving composition can be added as a liquid preparation or in the form of a dry powder composition either comprising the enzyme as the sole active component or in admixture with one or more other dough ingredients or additive.

The amount of the enzyme component added normally is an amount which results in the presence in the finished dough of 1 to 10,000 units per kg of flour, preferably 5 to 5000 units such as 10 to 1000 units. In useful embodiments, the amount is in the range of 20 to 500 units per kg of flour. In the present context 1 oxidoreductase unit corresponds to the amount of enzyme which under specified conditions results in the conversion of 1 μmole glucose per minute. The activity is stated as units per g of enzyme preparation.

Rheological Properties

The phrase "rheological properties" as used herein relates to the physical and chemical phenomena described herein which in combination will determine the performance of flour doughs and thereby also the quality of the resulting products.

The phrase "machineability of a flour dough" as used herein refers to the improved manipulation by machinery of the dough. The dough is less sticky compared to the dough without the addition of the combination.

In a further embodiment, the invention relates to improvement of the rheological characteristics of the dough including that the gluten index in the dough is increased by at least 5%, relative to a dough without addition of a combination, the gluten index is determined by means of a Glutomatic 2200 apparatus.

The phrase "rheological properties" as used herein refers to the effects of dough conditioners on dough strength and stability as the most important characteristics of flour doughs. According to American Association of Cereal Chemists (AACC) Method 36-01A the term "stability" can be defined as "the range of dough time over which a positive response is obtained and that property of a rounded dough by which it resists flattening under its own weight over a course of time". According to the same method, the term "response" is defined as "the reaction of dough to a known and specific stimulus, substance or set of conditions, usually determined by baking it in comparison with a control".

As it is mentioned herein, it is generally desirable to improve the baking performance of flour to achieve a dough with improved stretchability and thus having a desirable strength and stability by adding oxidising agents which cause the formation of protein disulphide bonds whereby the protein forms a more stable matrix resulting in a better dough quality and improvements of the volume and crumb structure of baked products.

The effect of the oxidoreductase or the dough improving composition on the rheological properties of the dough can be measured by standard methods according to the International Association of Cereal Chemistry (ICC) and the American Association of Cereal Chemistry (AACC) including the amylograph method (ICC 126), the farinograph method (AACC 54-21) and the extensigraph method (AACC 54-10). The extensigraph method measures e.g. the doughs ability to retain gas evolved by yeast and the ability to withstand proofing. In effect, the extensigraph method measures the relative strength of a dough. A strong dough exhibits a higher and, in some cases, a longer extensigraph curve than does a weak dough. AACC method 54-10 defines the extensigraph in the following manner: "the extensigraph records a load-extension curve for a test piece of dough until it breaks. Characteristics of load-extension curves or extensigrams are used to assess general quality of flour and its responses to improving agents".

In a preferred embodiment of the invention, the resistance to extension of the dough in terms of the ratio between the resistance to extension (height of curve, B) and the extensibility (length of curve, C), i.e. the B/C ratio as measured by the AACC method 54-10 is increased by at least 10% relative to that of an otherwise similar dough not containing oxidoreductase. In more preferred embodiments, the resistance to extension is increased by at least 20%, such as at least 50% and in particular by at least 100%.

The method according to the invention can be used for any type of flour dough with the aims of improving the rheologi-cal properties hereof and the quality of the finished prod-ucts made from the particular type of dough. Thus, the method is highly suitable for the making of conventional types of yeast leavened bread products including wheat flour based bread products such as loaves and rolls. However, it is contemplated that the method also can improve the properties of doughs in which leavening is caused by the addition of chemical leavening agents, including sweet bakery products such as cake products including as examples pound cakes and muffins, or scones.

Noodles

In one interesting aspect, the invention is used to improve the rheological properties of doughs intended for noodle products including "white noodles" and "chinese noodles" and to improve the textural qualities of the finished noodle products. A typical basic recipe for the manufacturing of noodles comprises the following ingredients: wheat flour 100 parts, salt 0.5 parts and water 33 parts. Furthermore, glycerol is often added to the noodle dough. The noodles are typically prepared by mixing the ingredients in an appropriate mixing apparatus followed by rolling out the noodle dough using an appropriate noodle machine to form the noodle strings which are subsequently air dried.

The quality of the finished noodles is assessed inter alia (i.a.) by their colour, cooking quality and texture. The noodles should cook as quickly as possible, remain firm after cooking and should preferably not loose any solids to the cooking water. On serving the noodles should preferably have a smooth and firm surface not showing stickiness and provide a firm "bite" and a good mouthfeel. Furthermore, it is important that the noodles have a light colour.

Since the appropriateness of wheat flour for providing noodles having the desired textural and eating qualities may vary according to the year and the growth area, it is usual to add noodle improvers to the dough in order to compensate for sub-optimal quality of the flour. Typically, such improvers will comprise dietary fiber substances, vegetable proteins, emulsifiers and hydrocolloids such as e.g. alginates, carrageenans, pectins, vegetable gums including guar gum and locust bean gum, and amylases, and glycerol.

It has been attempted to use glucose oxidase as a noodle improving agent. However, as mentioned above, the content of glucose may be so low in wheat flour that this enzyme will not be effective.

It is therefore an important aspect of the invention that the oxidoreductase according to the invention and the composition according to the invention is useful as a noodle improving agent, optionally in combination with glycerol and other components currently used to improve the quality of noodles. Thus, it is contemplated that noodles prepared in accordance with the above method will have improved properties with respect to colour, cooking and eating qualities including a firm, elastic and non-sticky texture and consistency.

Alimentary Paste Product

In a further useful embodiment the dough which is prepared by the method according to the invention is a dough for preparing an alimentary paste product. Such products which include as examples spaghetti and maccaroni are typically prepared from a dough comprising as the main ingredients such as flour, eggs or egg powder and/or water. After mixing of the ingredient, the dough is formed to the desired type of paste product and air dried. It is contemplated that the addition of the combination to a paste dough, optionally in combination with its substrate, will have a significant improving effect on the extensibility and stability hereof resulting in finished paste product having textural and eating qualities.

In a further aspect of the invention there is provided a dough improving composition comprising the oxidoreductase according to the invention and at least one further dough ingredient or dough additive.

Bread

In the invention the improvement of the rheological properties of the dough include that the resistance to extension of the dough in terms of the ratio between resistance to extension (height of curve, B) and the extensibility (length of curve, C), i.e. the B/C ratio, as measured by the AACC method 54-10 is increased by at least 10% relative to that of an otherwise similar dough that does not comprise the combination and wherein the improvement of the quality of the finished product made from the dough is that the average pore diameter of the crumb of the bread made from the dough is reduced by at least 10%, relative to a bread which is made from a bread dough without addition of the combination.

In a further embodiment, the invention, implies that the improvement of the quality of the product made from the dough consists in that the pore homogeneity of the crumb of the bread made from the dough is increased by at least 5%, relative to a bread which is made from a bread dough without addition of the combination. The pore homogeneity of bread is conveniently measured by means of an image analyser composed of a standard CCD-video camera, a video digitiser and a personal computer with WinGrain software. Using such an analyzer, the results of pore diameter in mm and pore homogeneity can be calculated as an average of measurements from 10 slices of bread. The pore homogeneity is expressed in % of pores that are larger than 0.5 times the average of pore diameter and smaller than 2 times the average diameter.

Preferably, the dough is a yeast leavened dough. Although, it is preferred to use the method of the present invention for the manufacture of yeast leavened bread products such as bread loaves, rolls or toast bread, the use of the method for any other type of dough and dough based products such as noodle and pasta products and cakes, the quality of which can be improved by the addition of the combination according to the present invention, is also contemplated.

Preferably the method comprises a further step that the dough is baked to obtain a baked product.

Preferably, when the dough is a bread dough, the method comprises as a further step that the dough is baked to obtain a baked product. One particularly desired property of baked bread products is a high specific volume as defined in the examples. Accordingly, the addition of the combination of the invention preferably results in an increase of the specific volume of the baked product that is at least 10%, relative to a baked product made under identical conditions except that the enzyme is not added. More preferably, the increase of the specific volume is at least 20% such as at least 30%, e.g. at least 40%. Alternatively, the dough is a dough selected from the group consisting of a pasta dough, a noodle dough, and a cake dough or batter.

The phrase "quality of the product" as used herein refers to the final and stable volume and/or crust colour and/or texture and taste.

The term "product made from dough" as used herein refers to a bread product such as in the form of loaves or rolls, french baguette type bread, pita bread, tacos and crisp bread. Preferably the term refers to cakes, pan-cakes, biscuits. More preferably the term refers to pasta. More preferably the term refers to noodles. More preferably the term refers to alimentary paste product.

In a preferred embodiment, the oxidoreductase is hexose oxidase. The further ingredients or additive can be any of the ingredients or additives which are described above. The composition may conveniently be a liquid preparation comprising the oxidoreductase. However, the composition is conveniently in the form of dry composition. It will be understood that the amount of oxidoreductase activity in the composition will depend on the types and amounts of the further ingredients or additives. However, the amount of oxidoreductase activity is preferably in the range of 10 to 100,000 units, preferably in the range of 100 to 50,000 units such as 1,000 to 10,000 units including 2,000 to 5,000 units.

Optionally, the composition may be in the form of a complete dough additive mixture or pre-mixture for a making a particular finished product and containing all of the dry ingredients and additives for such a dough. In specific embodiments, the composition may be one particularly useful for preparing a baking product or in the making of a noodle product or an alimentary paste product.

As mentioned above, the present invention provides a method for preparing a bakery product including the addition to the dough of an oxidoreductase such as e.g. hexose oxidase. In particular, this method results in bakery products such as the above mentioned products in which the specific volume is increased relative to an otherwise similar bakery product, prepared from a dough not containing oxidoreductase. It has been found that the addition of the composition of the present invention to bakery product doughs results in bakery products such as yeast leavened and chemically leavened products in which the specific volume is increased relative to an otherwise similar bakery product. In this context, the expression "specific volume" is used to indicate the ratio between volume and weight of the product. It has been found that, in accordance with the method described herein, the specific volume can be increased significantly such as by at least 10%, preferably by at least 20%, including by at least 30%, preferably by at least 40% and more preferably by at least 50%.

The present invention is highly suitable for improving the rheological and/or machineability properties and/or quality (e.g. volume) of the finished products (products made from the dough) of conventional types of yeast leavened bread products based on wheat flour, such as loaves and rolls. The present invention is also suitable for improving the rheological properties of doughs containing chemical leavening agents (baking powder) and the quality (e.g. volume) of products made from such doughs. Such product include as examples breads, sponge cakes and muffins.

Enzyme Amount

Preferably the or each enzyme is added in an amount from 1–1000 ppm, preferably 25–500 ppm, more preferably 50–300 ppm.

Nucleotide Sequence

The enzyme need not be a native enzyme. In this regard, the term "native enzyme" means an entire enzyme that is in its native environment and when it has been expressed by its native nucleotide sequence.

The nucleotide sequence of the present invention may be prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215–23 and Horn T et al (1980) Nuc Acids Res Symp Ser 225–232).

Amino Acid Sequences

The enzyme may be prepared/isolated from a suitable source, or it may be made synthetically or it may be prepared by use of recombinant DNA techniques.

Variants/Homologues/Derivatives

The present invention also encompasses the use of variants, homologues and derivatives of any amino acid sequence of an enzyme of the present invention or of any nucleotide sequence encoding such an enzyme. Here, the term "homologue" means an entity having a certain homology with the subject amino acid sequences and the subject nucleotide sequences. Here, the term "homology" can be equated with "identity".

In the present context, an homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

The invention will now be described by way of illustration in the following non-limiting examples and the drawings, in which:

FIG. 1 which is a photographic image of a bread;
FIG. 2 which is a photographic image of a bread; and
FIG. 3 which is a photographic image of a bread.

EXAMPLE 1

1.1. Purification of Hexose Oxidase from *Chondrus crispus*

A purified hexose oxidase preparation was obtained using the below extraction and purification procedures. During these procedures and the following characterizations of the purified enzyme, the following assay for determination of hexose oxidase activity was used:

1.1.1. Assay of Hexose Oxidase Activity

The assay was based on the method described by Sullivan and Ikawa (Biochimica et Biophysica Acta, 1973, 309:11–22), but modified to run in microtiter plates. An assay mixture contained 150 µl β-D-glucose (0.1 M in 0.1 M sodium phosphate buffer, pH 6.3), 120 µl 0.1 M sodium phosphate buffer, pH 6.3, 10 µl o-dianisidine-dihydrochloride (Sigma D-3252, 3.0 mg/ml in $H_2O$), 10 µl peroxidase (POD) (Sigma P-8125, 0.1 ml in 0.1 M sodium phosphate buffer, pH 6.3) and 10 µl enzyme (HOX) solution. Blanks were made by adding buffer in place of enzyme solution.

The incubation was started by the addition of glucose. After 15 minutes of incubation at 25° C. the absorbance at 405 nm was read in an ELISA reader. A standard curve was constructed using varying concentrations of $H_2O_2$ in place of the enzyme solution.

The reaction can be described in the following manner:

HOX

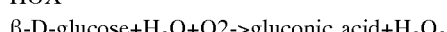

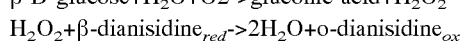

Oxidized o-dianisidine has a yellow colour absorbing at 405 nm.

1.1.2. Extraction

Fresh *Chondrus crispus* fronds were harvested along the coast of Brittany, France. This fresh material was homogenized in a pin mill (Alpine). To a 100 g sample of the resulting homogenized frond material was added 300 ml of 0.1 M sodium phosphate buffer, pH 6.8. The mixture was subsequently sonicated in a sonication bath for 5 minutes and then extracted under constant rotation for 4 days at 5° C., followed by centrifugation of the mixture at 47,000×g for 20 minutes.

300 ml of the resulting clear pink supernatant was desalted by ultrafiltration using an Amicon ultrafiltration unit equipped with an Omega (10 kD cut off, Filtron) ultrafiltration membrane.

1.1.3. Anion Exchange Step

The retentate resulting from 1.1.2 was applied to a 5×10 cm column with 200 ml Q-Sepharose FF equilibrated in 20 mM triethanolamine, pH 7.3. The column was washed with the equilibration buffer and hexose oxidase eluted with a 450 ml gradient of 0 to 1 M of NaCl in equilibration buffer. The column was eluted at 6 ml/minute, and fractions of 14 ml collected. Fractions 9–17 (total 125 ml) were pooled and concentrated by ultrafiltration using an Amicon 8400 unit equipped with an Omega (10 kD cut off, Filtron) ultrafiltration membrane to 7.5 ml.

1.1.4. Gel Filtration

The above 7.5 ml retentate was applied to a Superdex 200 2.6×60 cm gel filtration column equilibrated in 50 mM sodium phosphate buffer, pH 6.4 and eluted at a flow rate of 1 ml/-minute. Fractions of 4 ml were collected. Fractions 17–28 (total volume 50 ml) containing the hexose oxidase activity were pooled.

1.1.5. Hydrophobic Interaction Chromatography

To the pool resulting from the gel filtration step 1.1.4 ammonium sulphate was added to a final concentration of 2 M. This mixture was then applied to a 1.6×16 cm column with 32 ml phenyl sepharose equilibrated in 20 mM sodium phosphate buffer, pH 6.3 and 2 M $(NH_4)_2SO_4$. The column was washed with equilibration buffer followed by elution of hexose oxidase at a flow rate of 2 ml/minute using a 140 linear gradient from 2 M to 0 M $(NH_4)_2SO_4$ in 20 mM sodium phosphate buffer. Fractions of 4 ml were collected and fractions 24–33 containing the hexose oxidase activity were pooled.

The above mentioned pink colour accompanies the enzyme, but it is separated from hexose oxidase in this purification step.

1.1.6. Mono Q Anion Exchange

The above pool resulting from the above phenyl sepharose chromatography step was desalted by ultrafiltration as described above. 2 ml of this pool was applied to a Mono Q HR 5/5 column equilibrated in 20 mM triethanolamine, pH 7.3. The column was subsequently eluted using a 45 ml linear gradient from 0 to 0.65 M NaCl in equilibration buffer at a flow rate 1.5 ml/minute. Fractions of 1.5 ml were collected and fractions 14–24 were pooled.

1.1.7. Mono P Anion Exchange

The hexose oxidase-containing pool from the above step 1.1.6 was applied to a Mono P HR 5/5 column equilibrated in 20 mM bis-Tris buffer, pH 6.5. The enzyme was eluted using a 45 ml linear gradient from 0 to 0.65 M NaCl in equilibration buffer at a flow rate of 1.5 ml/minute, and fractions of 0.75 ml were collected. The highest hexose oxidase activity was found in fraction 12.

1.2. Characterization of the Purified Hexose Oxidase

The hexose oxidase-containing pools from the above steps 1.1.6 and 1.1.7 were used in the below characterization experiments:

1.2.1. Determination of Molecular Weight

The size of the purified native hexose oxidase was determined by gel permeation chromatography using a Superose 6 HR 10/30 column at a flow rate of 0.5 ml/minute in 50 mM sodium phosphate buffer, pH 6.4. Ferritin (440 kD), catalase (232 kD), aldolase (158 kD), bovine serum albumin (67 kD) and chymotrypsinogen (25 kD) were used as size standards. The molecular weight of the purified hexose oxidase was determined to be 120+10 kD.

1.2.2. Determination of pH Optimum

Assay mixtures for the determination of pH optimum (final volume 300 $\mu$l) contained 120 $\mu$l of 0.1 M stock solution of sodium phosphate/citrate buffer of varying pH values. All other assay mixture components were dissolved in $H_2O$. The pH was determined in the diluted stock buffer solutions at 25° C. The hexose oxidase showed enzymatic activity from pH 3 to pH 8, but with optimum in the range of 3.5 to 5.5.

1.2.3. $K_m$ of the Hexose Oxidase for Glucose and Maltose Respectively

Kinetic data were fitted to $V=V_{max}S/(Km+S)$, where $V_{max}$ is the maximum velocity, S is the substrate concentration and Km is the concentration giving 50% of the maximum rate (Michaelis constant) using the EZ-FIT curve fitting microcomputer programme (Perrella, F. W., 1988, Analytical Biochemistry, 174:437–447).

A typical hyperbolic saturation curve was obtained for the enzyme activity as a function of glucose and maltose, respectively. $K_m$ for glucose was calculated to be 2.7 mM±0.7 mM and for maltose the $K_m$ was found to be 43.7±5.6 mM.

EXAMPLE 2

Dough Improving Effect of Hexose Oxidase Extracted from *Chondrus crispus*

2.1. Purification of Hexose Oxidase from *Chondrus crispus*

For this experiment, hexose oxidase was prepared in the following manner:

Fresh *Chondrus crispus* material was collected at the coast of Brittany, France. The material was freeze-dried and subsequently ground. 40 g of this ground material was suspended in 1000 ml of 20 mM triethanolamine (TEA) buffer, pH 7.3 and left to stand at 5° C. for about 64 hours with gentle agitation and then centrifuged at 2000×g for 10 minutes. The supernatant was filtered through GF/A and GF/C glass filters followed by filtering through a 45 $\mu$m pore size filter to obtain a filtrate preparation of 800 ml having hexose oxidase activity corresponding to a glucose oxidase activity of 0.44 units per g of preparation. The activity was determined using the below procedure.

The supernatant was applied onto a 330 ml bed volume chromatographic column with anionic exchange Q Sepharose Big Beads (dead volume 120 ml). The bound proteins were eluted over 180 minutes using a gradient from 0 to 0.5 M NaCl in 20 mM TEA buffer, pH 7.3 followed by 1 M NaCl in 20 mM TEA buffer, and fractions of 9 ml were collected and analyzed for hexose oxidase activity using the below analytical procedure.

Hexose oxidase activity-containing fractions 60–83 were pooled (about 250 ml) and concentrated and desalted by ultrafiltration to about 25 ml. This step was repeated twice on the retentates to which was added 100 ml 0.05 mM TEA. The resulting retentate of 25 ml contained 0.95 glucose oxidase activity units per g.

2.2. Determination of Glucose Oxidase Activity

Definition: 1 glucose oxidase (GOD) unit corresponds to the amount of enzyme which under the specified conditions results in the conversion of 1 $\mu$mole glucose per min. The activity is stated as units per g of enzyme preparation.

Reagents: (i) Buffer: 20 g $Na_2HPO_4$-$2H_2O$ is dissolved in 900 ml distilled water, pH is adjusted to 6.5; (ii) dye reagent (stock solution): 200 mg of 2,6-dichloro-phenol-indophenol, Sigma No. D-1878 is dissolved in 1000 ml distilled water under vigorous agitation for 1 hour; (iii) peroxidase (stock solution): Boehringer Mannheim No. 127 361, 10,000 units is dissolved in 10 ml distilled water and 4.2 g of ammonium sulphate added; (iv) substrate: 10% w/v D-glucose solution in buffer, (v) standard enzyme: hydrase #1423 from Amano.

Analytical principle and procedure: Glucose is converted to gluconic acid and $H_2O_2$ which is subsequently converted by peroxidase to $H_2O$ and $O_2$. The generated oxygen oxidizes the blue dye reagent 2,6-dichloro-phenol-indophenol which thereby changes its colour to purple. The oxidized colour is measured spectrophotometrically at 590 nm and the enzymatic activity values calculated relative to a standard.

2.3. The Effect of the Hexose Oxidase Preparation on Crosslinking between Thiol Groups in a Wheat Flour Based Dough The effect of hexose oxidase on the formation of thiol group cross-linking was studied by measuring the content of free thiol groups in a dough prepared from 1500 g of wheat flour, 400 Brabender Units (BU) of water, 90 g of yeast, 20 g of sucrose and 20 g of salt to which was added 0, 100, 250, 875 and 1250 units per kg of flour, respectively of the above hexose oxidase preparation. The measurement was carried out essentially in accordance with the colorimetric method of Ellman (1958) as also described in Cereal Chemistry, 1983, 70, 22–26. This method is based on the principle that 5.5'-dithio-bis(2-nitrobenzoic acid) (DTNB) reacts with thiol groups in the dough to form a highly coloured anion of 2-nitro-5-mercapto-benzoic acid, which is measured spectrophotometrically at 412 nm.

Assuming that the relative change of the amount of thiol groups in a dough is reflected as the change in the optical density (OD) resulting from the reaction between thiol groups and DTNB in the dough, the following results were obtained:

| Hexose oxidase GOD units/kg flour | $OD_{412}$ |
|---|---|
| 0 | 0.297 |
| 100 | 0.285 |
| 250 | 0.265 |
| 875 | 0.187 |
| 1250 | 0.138 |

Thus, this experiment showed a significant decrease in OD indicating a reduction of the content of free thiol groups which was proportionate to the amount of hexose oxidase activity added.

2.4. Improvement of the Rheological Characteristics of Dough by the Addition of Hexose Oxidase The above dough was subjected to extensigraph measurements according to AACC Method 54-10 with and without the addition of an amount of the hexose oxidase preparation corresponding to 100 units/kg flour of hexose oxidase activity. The dough without addition of enzyme served as a control.

The principle of the above method is that the dough after forming is subjected to a load-extension test after resting at 30° C. for 45, 90, 135 and 180 minutes, respectively, using an extensigraph capable of recording a load-extension curve (extensigram) which is an indication of the doughs resistance to physical deformation when stretched. From this curve, the resistance to extension, B (height of curve) and the extensibility, C (total length of curve) can be calculated. The B/C ratio (D) is an indication of the baking strength of the flour dough.

The results of the experiment is summarized in Table 2.1 below.

TABLE 2.1

Extensigraph measurements of dough supplemented with 100 GOD units/kg flour of hexose oxidase (HOX).

| Sample | Time, min | B | C | D = B/C |
|---|---|---|---|---|
| Control | 45 | 230 | 180 | 1.3 |
| HOX | 45 | 320 | 180 | 1.8 |
| Control | 90 | 290 | 161 | 1.8 |
| HOX | 90 | 450 | 148 | 3.0 |
| Control | 135 | 290 | 167 | 1.7 |
| HOX | 135 | 490 | 146 | 3.4 |
| Control | 180 | 300 | 168 | 1.8 |
| HOX | 180 | 500 | 154 | 3.2 |

It is apparent from this table that the addition of hexose oxidase (HOX) has an improving effect on the doughs resistance to extension as indicated by the increase in B-values. This is reflected in almost a doubling of the B/C ratio as a clear indication that the baking strength of the flour is significantly enhanced by the hexose oxidase addition.

In a similar experiment, 100 units/kg flour of a commercial glucose oxidase product was added and the above parameters measured in the same manner using a dough without enzyme addition as a control. The results of this experiment is shown in Table 2.2 below:

TABLE 2.2

Extensigraph measurements of dough supplemented with 100 GOD units/kg flour of glucose oxidase (GOX).

| Sample | Time, min | B | C | D = B/C |
|---|---|---|---|---|
| Control | 45 | 240 | 180 | 1.3 |
| GOX | 45 | 290 | 170 | 1.7 |
| Control | 90 | 260 | 175 | 1.5 |
| GOX | 90 | 360 | 156 | 2.3 |
| Control | 135 | 270 | 171 | 1.6 |
| GOX | 135 | 420 | 141 | 3.0 |

When the results for the above two experiments are compared with regard to differences between control dough and the hexose oxidase or glucose oxidase supplemented doughs it appeared that hexose oxidase has a stronger strengthening effect than glucose oxidase. Furthermore, the B/C ratio increased more rapidly with hexose oxidase relative to glucose oxidase which is a clear indication that enhancement of the baking strength is being conferred more efficiently by hexose oxidase than by glucose oxidase.

EXAMPLE 3

Dough Improving Effect of Hexose Oxidase Extracted from *Chondrus crispus*

For this experiment fresh *Chondrus crispus* seaweed fronds were harvested along the coast of Hirsholmene, Denmark. Hexose oxidase was isolated using two different extraction procedures, and the materials from both were pooled for the below dough improving experiment.

3.1. Purification of Hexose Oxidase from *Chondrus crispus* I 954 g of the fresh fronds was rinsed in distilled water, dried with a towel and stored in liquid nitrogen. The seaweed was blended using a Waring blender and 1908 ml of 0.1 M sodium phosphate buffer, 1 M NaCl, pH 6.8 was added to the blended seaweed. The mixture was extracted under constant stirring for 4 days at 5° C., followed by centrifugation of the mixture at 20,000×g for 30 minutes.

The resulting 1910 ml supernatant (351.1 U/ml) was concentrated to 440 ml at 40° C. in a Buchi Rotavapor R110. The concentrate was ammonium sulphate fractionated to 25% The mixture was stirred for 30 minutes and centrifuged for 20 minutes at 47,000×g. The supernatant (395 ml) was dialysed overnight against 20 l of 10 mM triethanolamine (TEA) buffer, pH 7.3 to a final volume of 610 ml (367.1 U/ml).

The above 610 ml was applied in two runs to a 2.6×25 cm column with 130 ml Q-Sepharose FF equilibrated in 20 mM TEA buffer, pH 7.3. The column was washed with the equilibration buffer and the bound proteins were eluted using 800 ml gra dient from 0 to 0.8 M NaCl in equilibration buffer. The column was eluted at 4 ml/minute and fractions of 12 ml collected. Fractions containing the hexose oxidase activity were collected and pooled to a final volume of 545 ml (241.4 U/ml).

3.2. Purification of Hexose Oxidase from *Chondrus crispus* II 1250 g of the fresh fronds was rinsed in distilled water, dried with a towel and stored in liquid nitrogen. The seaweed was blended in a Waring blender followed by the addition of 2500 ml 0.1 M sodium phosphate buffer, 1 M NaCl. pH 6.8. The mixture was extracted under continuous stirring for 4 days at 5° C. followed by centrifugation at 20,000×g for 30 minutes.

The resulting 2200 ml supernatant (332.8 U/ml) was concentrated to 445 ml at 40° C. using a Buchi Rotavapor R110. The resulting concentrate was ammonium sulphate fractionated to 25%. The mixture was stirred for 30 minutes and centrifuged for 20 minutes at 47,000×g. The precipitate was discarded. The 380 ml supernatant was dialysed overnight against 20 l 10 mM TEA buffer, pH 7.3, to a final volume of 850 ml (319.2 U/ml).

The above 850 ml was applied to a 2.6×25 cm column with 130 ml Q-Sepharose FF equilibrated in 20 mM TEA buffer, pH 7.3.

The column was washed with the equilibration buffer and the bound proteins were eluted using 800 ml gradient from 0 to 0.8 M NaCl in equilibration buffer. The column was eluted at 4 ml/minute and fractions of 12 ml collected. Fractions containing the hexose oxidase activity were collected and pooled to a final volume of 288 ml.

The retentate from the above step was applied to a 2.6×31 cm column with 185 ml metal chelating sepharose FF loaded with $Ni^{2+}$ and equilibrated in 50 mM sodium phosphate, 1 M NaCl, pH 7.4. The bound proteins were eluted with a 740 ml gradient of 0 to 35 mM imidazole, pH 4.7 in equilibration buffer. The column was eluted at 2 ml/minute and fractions of 11 ml was collected. Fractions 41–54 (140 ml, 352.3 U/ml) were pooled. Some hexose oxidase did run through the column.

3.3. Pooling and Concentrating of Extracts

The run through and the 140 ml from purification II and the 545 ml from purification I were pooled to a final volume of 1120 ml (303.6 U/ml). The 1120 ml was rotation evaporated into a volume of 210 ml followed by dialysis overnight against 20 l of 10 mM TEA buffer, pH 7.3, to a final volume of 207 ml (1200.4 U/ml)

3.3.1. Anion Exchange Step

The retentate resulting from the above step was applied to a 2.6×25 cm column with 130 ml Q-sepharose FF equilibrated in 20 mM triethanolamine, pH 7.3. The column was washed with the equilibration buffer and the bound proteins eluted using 800 ml gradient from 0 to 0.8 M NaCl in equilibration buffer. The column was eluted at 4 ml/minute and fractions of 12 ml collected. Fractions 30–50 containing the hexose oxidase activity (260 ml, 764.1 U/ml) were collected and pooled.

3.3.2. Other Enzyme Activity

The above pooled solution was tested for the following enzymatic side activities catalase, protease, xylanase, α- and β-amylase and lipase. None of these activities were found in the solution.

3.4. Improvement of the Rheological Characteristics of Dough by the Addition of Hexose Oxidase A dough was prepared from wheat flour, water and salt and 0, 72, 216 and 360 units per kg of flour, respectively of the above hexose oxidase preparation was added hereto. The dough without addition of enzyme served as a control. In addition two doughs were prepared to which was added 216 and 360 units per kg of flour respectively, of Gluzyme, a glucose oxidase available from Novo Nordisk A/S. Denmark.

The doughs were subjected to extensigraph measurements according to a modification of the above AACC Method 54-10. The results of the experiment are summarized in Table 3.1 below.

TABLE 3.1

Extensigraph measurements of dough supplemented with hexose oxidase (HOX) or glucose oxidase (units per kg flour)

| Sample | Time, Min | B | C | D = B/C |
|---|---|---|---|---|
| Control | 45 | 250 | 158 | 1.6 |
| HOX 72 U/kg | 45 | 330 | 156 | 2.1 |
| HOX 216 U/kg | 45 | 460 | 153 | 3.0 |
| HOX 360 U/kg | 45 | 580 | 130 | 4.5 |
| Gluzyme 72 U/kg | 45 | 350 | 159 | 2.2 |
| Gluzyme 216 U/kg | 45 | 340 | 148 | 2.3 |
| Gluzyme 360 U/kg | 45 | 480 | 157 | 3.1 |
| Control | 90 | 290 | 164 | 1.8 |
| HOX 72 U/kg | 90 | 470 | 145 | 3.2 |
| HOX 216 U/kg | 90 | 650 | 142 | 4.6 |
| HOX 360 U/kg | 90 | 870 | 116 | 7.5 |
| Gluzyme 72 U/kg | 90 | 450 | 147 | 3.1 |
| Gluzyme 216 U/kg | 90 | 480 | 138 | 3.5 |
| Gluzyme 360 U/kg | 90 | 500 | 152 | 3.2 |
| Control | 135 | 330 | 156 | 2.1 |
| HOX 72 U/kg | 135 | 540 | 129 | 4.2 |
| HOX 216 U/kg | 135 | 750 | 125 | 6.0 |
| HOX 360 U/kg | 135 | 880 | 117 | 7.5 |
| Gluzyme 72 U/kg | 135 | 510 | 136 | 3.8 |
| Gluzyme 216 U/kg | 135 | 550 | 122 | 4.5 |
| Gluzyme 360 U/kg | 135 | 560 | 121 | 4.6 |

It is evident from the above table that the addition of hexose oxidase (HOX) or glucose oxidase had an improving effect on the resistance of doughs to extension as indicated by the increase in B-values. This is reflected in an increase of the B/C ratio as a clear indication that the baking strength of the flour was enhanced significantly by the addition of enzymes.

It is also evident that the hexose oxidase had a higher strengthening effect than glucose oxidase. Furthermore, the B/C ratio increased more rapidly with hexose oxidase relative to glucose oxidase which is a clear indication that enhancement of the baking strength is being conferred more efficiently by hexose oxidase than by glucose oxidase.

EXAMPLE 4

Dough Improving Effect of Hexose Oxidase Extracted from *Chondrus crispus*

4.1. Purification of Hexose Oxidase from *Chondrus crispus*

Fresh *Chondrus crispus* fronds were harvested along the coast of Brittany, France. 2285 g of this fresh material was rinsed in distilled water, dried with a towel and stored in liquid nitrogen. The seaweed was blended in a Waring blender followed by addition of 4570 ml 0.1 M sodium phosphate buffer, 1 M NaCl pH 6.8. The mixture was extracted under continuous magnetic stirring for 4 days at 5° C. followed by centrifugation at 20,000×g for 30 minutes.

The resulting 4930 ml supernatant (624.4 U/ml) was concentrated to 1508 ml at 40° C. using a Buchi Rotavapor R110. The obtained concentrate was polyethylenglycol fractionated to 3% (w/v). The mixture was stirred for 30 minutes and centrifuged for 30 minutes at 47,000×g. The pellet was discarded. The 1470 ml supernatant (2118.7 U/ml) was PEG fractionated to 24%. The mixture was stirred for 30 minutes and centrifuged for 30 minutes at 47,000×g. The supernatant was discarded and the 414.15 g of precipitate was resuspended in 200 ml 20 mM TEA buffer, pH 7.3, followed by dialysis over night at 5° C. against 20 l 10 mM TEA buffer, pH 7.3.

After dialysis the volume was 650 ml (2968.6 U/ml). The suspension was centrifuged for 30 minutes at 20,000×g. The precipitate was discarded and the supernatant was diluted to 3200 ml with distilled water.

The above 3200 ml (829.9 U/ml) was applied to a 10×14 cm column with 1100 ml Q-Sepharose FF equilibrated in 20 mM TEA buffer, pH 7.3. The column was washed with the equilibration buffer and the bound proteins were eluted using 15,000 ml gradient from 0 to 0.8 M NaCl in equilibration buffer. The column was eluted at 50 ml/minute. Hexose oxidase did run through the column and 840 ml of this was collected.

The 840 ml suspension was treated with kieselguhr and concentrated to 335 ml (2693.3 U/ml).

The above 335 ml was applied to a 3 l Sephadex G25C desalting column 10×40 cm. The column was equilibrated in 20 mM TEA buffer, pH 7.3, eluted at a flow rate of 100 ml/minute and 970 ml eluate was collected. This eluate was applied to a 10×14 cm column with 1100 ml Q-Sepharose FF equilibrated in 20 mM TEA, pH 7.3. The column was washed with the equilibration buffer and bound proteins eluted using a 15,000 ml gradient of 0 to 0.8 M NaCl in equilibration buffer. The column was eluted at 50 ml/min. Hexose oxidase did run through the column and 1035 ml of this was collected.

To the above eluate (1035 ml) ammonium sulphate was added to a final concentration of 2 M. The mixture was then applied in two runs to a 5×10 cm column with 200 ml phenyl sepharose HP equilibrated in 25 mM sodium phosphate buffer, pH 6.3 and 2 M $(NH_4)_2SO_4$. The column was washed with equilibration buffer followed by eluting the bound proteins at a flow rate of 50 ml/minute using 5,000 ml gradient from 2 M to 0 M $(NH_4)_2SO_4$ in 25 mM sodium phosphate buffer. Fractions of 500 and 29 ml, respectively were collected from run 1 and 2. Fraction 5 in run 1 and fractions 27–42 in run 2 containing the hexose oxidase activity were pooled to a total of 1050 ml (563.9 U/ml).

The above pool was desalted by a 3 l Sephadex G25C gel filtration column. The column was equilibrated in 20 mM TEA buffer, pH 7.3, eluted at a flow rate of 100 ml/minute and 1,000 ml eluate was collected.

The 1,000 ml eluate was concentrated to 202 ml (2310.2 U/ml) and this preparation was used for following rheology testing.

4.2. Improvement of the Rheological Characteristics of Dough by the Addition of Hexose Oxidase A dough was prepared from wheat flour, water and salt and 0, 288, 504 and 720 oxidoreductase units per kg of flour, respectively of the above hexose oxidase preparation was added hereto. The dough without addition of enzyme served as a control. In addition two doughs were prepared to which was added 288 and 504 oxidoreductase units per kg of flour respectively, of Gluzyme, a glucose oxidase available from Novo Nordisk A/S. Denmark.

The doughs were subjected to extensigraph measurements according to a modification of AACC Method 54-10.

The results of the experiment are summarized in Table 4.1 below.

TABLE 4.1

Extensigraph measurements of dough supplemented with hexose oxidase (HOX) or glucose oxidase (Units per kg flour).

| Sample | Time, Min | B | C | D = B/C |
|---|---|---|---|---|
| Control | 45 | 210 | 171 | 1.2 |
| HOX 288 U/kg | 45 | 490 | 139 | 3.5 |

TABLE 4.1-continued

Extensigraph measurements of dough supplemented with hexose oxidase (HOX) or glucose oxidase (Units per kg flour).

| Sample | Time, Min | B | C | D = B/C |
|---|---|---|---|---|
| HOX 504 U/kg | 45 | 640 | 122 | 5.2 |
| HOX 720 U/kg | 45 | 730 | 109 | 6.7 |
| Gluzyme 288 U/kg | 45 | 350 | 165 | 2.1 |
| Gluzyme 504 U/kg | 45 | 385 | 153 | 2.5 |
| Gluzyme 720 U/kg | 45 | 435 | 148 | 2.9 |
| Control | 90 | 275 | 182 | 1.5 |
| HOX 288 U/kg | 90 | 710 | 130 | 5.5 |
| HOX 504 U/kg | 90 | 825 | 106 | 7.8 |
| HOX 720 U/kg | 90 | 905 | 107 | 8.5 |
| Gluzyme 288 U/kg | 90 | 465 | 153 | 3.0 |
| Gluzyme 504 U/kg | 90 | 515 | 135 | 3.8 |
| Gluzyme 720 U/kg | 90 | 540 | 140 | 3.9 |
| Control | 135 | 280 | 175 | 1.6 |
| HOX 288 U/kg | 135 | 745 | 102 | 7.3 |
| HOX 504 U/kg | 135 | 920 | 94 | 9.8 |
| HOX 720 U/kg | 135 | — | 80 | — |
| Gluzyme 288 U/kg | 135 | 525 | 129 | 4.1 |
| Gluzyme 504 U/kg | 135 | 595 | 129 | 4.6 |
| Gluzyme 720 U/kg | 135 | 630 | 121 | 5.2 |

It is apparent from the above results that the addition of hexose oxidase (HOX) or glucose oxidase has an improving effect on the resistance of doughs to extension as indicated by the increase in B-values. This is reflected in an increase of the B/C ratio.

It is also apparent that hexose oxidase has a stronger s strengthening effect than that of glucose oxidase, the strengthening effect of both enzymes being proportional to the amount of enzyme added. Furthermore, the B/C ratio increased more rapidly with hexose oxidase relative to glucose oxidase which is a clear indication that enhancement of the baking strength is being conferred more efficiently by hexose oxidase than by glucose oxidase.

EXAMPLE 5

Improving Effect of Hexose Oxidase Extracted from *Chondrus crispus* on the Specific Volume of Bread 5.1. Purification of Hexose Oxidase from *Chondrus crispus*

Fresh *Chondrus crispus* fronds were harvested along the coast of Brittany, France. 2191 g of this fresh material was rinsed in distilled water, dried with a towel and stored in liquid nitrogen. The seaweed was blended in a Waring blender fol lowed by addition of 4382 ml 0.1 M sodium phosphate buffer, 1 M NaCl and pH 6.8. The mixture was extracted under continuously magnetic stirring for 4 days at 5° C. followed by centrifugation at 20,000×g for 20 minutes.

The resulting 4600 ml supernatant (746.1 U/ml) was concentrated to 850 ml at 40° C. in a Buchi Rotavapor R110. This concentrate (3626.9 U/ml) was polyethylene glycol fractionated to 3% (w/v). The mixture was stirred for 30 minutes and centrifuged for 30 minutes at 20,000×g. The precipitate was discarded. The 705 ml supernatant (2489.8 U/ml) was PEG fractionated to 25%. The mixture was stirred for 30 minutes and centrifuged for 30 minutes at 20,000×g. The supernatant was discarded and the 341 g of precipitate was resuspended in 225 ml 20 mM TEA buffer, pH 7.3. The suspension (500 ml) was desalted on a 3 l Sephadex G25C desalting column 10×40 cm. The column was equilibrated in 20 mM TEA buffer, pH 7.3, and eluted at a flow rate of 100 ml/minute. 1605 ml eluate was collected.

To the above eluate (687.5 U/ml) ammonium sulphate was added to a final concentration of 2M. The mixture was then applied in two runs to a 5×10 cm column with 200 ml phenyl sepharose HP equilibrated in 25 mM sodium phosphate buffer, pH 6.3 and 2 M $(NH_4)_2SO_4$. The column was washed with equilibration buffer followed by elution of the bound proteins at a flow rate of 50 ml/minute using 5,000 ml gradient from 2 M to 0 M $(NH_4)_2SO_4$ in 25 mM sodium phosphate buffer. Fractions of 29 ml was collected. Fractions 85–105 in run 1 and fractions 36–69 in run 2 containing the hexose activity were pooled to a total of 1485 ml (194.7 U/ml).

The above pool was desalted by a 3 l Sephadex G25C gelfiltration column, the same as used in 4.1. The column was equilibrated in 20 mM TEA buffer, pH 7.3, and eluted at a flow rate of 100 ml/minute. 1,200 ml eluate was collected.

The 1,200 ml eluate was concentrated to 685 ml (726.2 U/ml) and used for baking experiments.

5.2. Improvement of the Specific Volume of Bread by Adding Hexose Oxidase to the Dough A dough was prepared from 1500 g of flour, 90 g of yeast, 24 g of salt, 24 g of sugar and 400 BU of water and 0 or 108 units of the above purified hexose oxidase and 108 units of Gluzyme (glucose oxidase available from Novo Nordisk, Denmark) per kg flour, respectively was added hereto. The dough was mixed on a Hobart mixer for 2+9 minutes at 26° C. and divided into two parts followed by resting for 10 minutes at 30° C. in a heating cabinet, moulding with a Fortuna 3/17/7 and proofing for 45 minutes at 34° C. and 85% RH. The thus proofed dough was baked at 220° C. for 17 minutes with 12 sec. steam in a Bago oven.

The results of the experiment are summarized in table 5.1 below.

TABLE 5.1

Improvement of specific volumes of bread prepared from dough supplemented with hexose oxidase or glucose oxidase (Units per kg flour)

|  | Total volume | Total weight | Specific volume |
|---|---|---|---|
| control | 5325 | 1027 | 5.18 |
| Hexose oxidase 108 U/kg | 6650 | 1036 | 6.41 |
| Gluzyme 108 U/kg | 6075 | 1030 | 5.89 |

It is evident from the above table that the addition of hexose oxidase or glucose oxidase had an increasing effect on the total volume, the weight being essentially the same. This is reflected in an increase of the specific volume as compared to the bread baked without addition of enzymes.

It is also evident that hexose oxidase has a significantly larger effect on the increase of the specific volume than had glucose oxidase at the same dosage.

EXAMPLE 6

Characterization of the Purified Hexose Oxidase

Preparations from the above purifications were used for characterization of hexose oxidase.

6.1. Staining for Hexose Activity After Non-Denaturing PAGE

Hexose oxidase activity was analyzed by native PAGE using precast 8–16% Tris-glycine Novex gels according to the manufactures instructions (Novex, San Diego, USA). After electrophoresis the gels were stained for hexose oxidase activity by incubation of the gel in a solution containing 50 mM sodium phosphate buffer, pH 6.0, 100 mM glucose, 50 mg/l phenazine methosulphate (Sigma P9625) and 250 mg/l nitroblue tetrazolium (Sigma N6876) as described in the PhD thesis by Witteveen, C. F. B. (1993) "Gluconate formation and polyol metabolism in *Aspergillus niger*". After about 30 minutes the hexose oxidase activity was visible as a double band very close to each other. The same double band was also seen when a native PAGE of hexose oxidase was silver stained. The molecular weight of purified hexose oxidase was determined to 144 kD by native PAGE. Half the gel was silver stained, the other half was activity stained. As standards were used bovine serum albumin (67 kD), lactate dehydrogenase (140 kD), catalase (232 kD), ferritin (440 kD) and thyroglobulin (669 kD).

6.2 Determination of Molecular Weight by SDS-Page

The molecular weight was also determined on material which was first applied to a native PAGE as described above, after activity staining the hexose oxidase band was excised from the gel and then electroeluted using an Electro-Eluter (model 422, Bio-Rad, CA, USA) according to the manufacturer's recommendations. The electroeluted protein was subjected to SDSPAGE and silver stained. This material gave "one" double band at about 70 kDa in SDS-PAGE gels. The electroeluted hexose oxidase is therefore a dimer of two subunits.

6.3 Determination of pI of Hexose Oxidase

Samples containing hexose oxidase activity were analyzed by isoelectric focusing (IEF) using a precast 3–10 IEF gel according to the manufacturer's recommendations (Novex, San Diego, US). After electrophoresis half of the gel was silver stained and the other half nitroblue tetrazolium stained as described in 6.1.

Hexose oxidase stained as a double band. The pI of the first band was 4.79, pI of the second band was 4.64. As standards were used trypsinogen (9.30), lentil lectin basic band (8.65), lentil lectin middle band (8.45), lentil lectin acid band (8.15), horse myoglobin acidic band (6.85), human carbonic anhydrase B (5.85), β-lactoglobulin A (5.20), soy bean trypsin inhibitor (4.55) and amyloglucosidase (3.50).

6.4 Determination of Km Hexose Oxidase for Different Sugars

Km of hexose oxidase was determined for 7 different sugars as described in 1.2.3. Results are summarized in table 6.1 below.

TABLE 6.1

Determination of Km of hexose oxidase for different sugars

| Substrate | Km (mM) | cv (mM) |
|---|---|---|
| D-glucose | 2.7 | 0.7 |
| D-galactose | 3.6 | 1 |
| cellobiose | 20.2 | 7.8 |
| maltose | 43.7 | 5.6 |
| lactose | 90.3 | 20.6 |
| xylose | 102 | 26 |
| arabinose | 531 | 158 |

(cv = coefficient of variation)

6.5 Determination of a Peptide Sequence of Hexose Oxidase

50 μl from the electroeluted mixture in 6.2 was suspended in 450 μl 0.1% triflouracetic acid (TFA).

To remove the Tris, glycine and SDS, the above mixture was subjected to chromatography on reverse-phase HPLC. The resulting solution was applied in 9 runs to a 4.6×30 cm Brownlee C2 column equilibrated in 0.1% TFA. The column was washed in equilibration buffer and bound peptides eluted with a 14 ml gradient from 10 to 80% acetonitrile in 0.1% TFA, at a flow rate of 0.7 ml/min. Fractions from the largest peak containing the enzyme were collected and freeze dried.

6.5.1 Endoproteinase Lys-C Digestion

The resulting freeze dried enzyme was dissolved in 50 µl 8 M urea, 0.4 M $NH_4HCO_3$, pH 8.4. Denaturation and reduction of the protein was carried out by the addition of 5 µl 45 mM di-thiothreitol and under an overlay of $N_2$ at 50° C. for 15 min. The solution was cooled to room temperature and 5 µl 100 mM iodoacetamide was added, the cysteines being derivatized for 15 min. at room temperature in the dark under $N_2$. Subsequently, the solution was suspended in 135 µl water and digestion was carried out at 37° C. under $N_2$ for 24 hours by addition of 5 µg endoproteinase Lys-C dissolved in 5 l water. The reaction was terminated by freezing the reaction mixture at −20° C.

6.5.2 Reverse-Phase HPLC Separation of Peptides

The resulting peptides were separated by reverse-phase HPLC on a VYDAC c18 column 0.46×15 cm (The Separation Group, CA, USA) using as solvent A 0.1% TFA in water and as solvent B 0.1% TFA in acetonitrile.

6.5.3 Peptide Sequencing

Sequencing was performed on an Applied Biosystems 476A sequencer (Applied Biosystems, CA, USA) using pulsed-liquid fast cycles according to the manufacturer's instructions. A peptide having the below amino acid sequence was identified:

D P C Y I V I D V N A G T P O K P D P.

EXAMPLES 7 TO 10

Definitions

All PANODAN™ products contain DATEM (Di-acetyl tartaric acid ester of monoglycerides) and are obtained from Danisco A/S.

PANODAN™ 521: DATEM containing bacterial xylanase and fungal amylase

TS-E 662™ (obtained from Danisco A/S) is a product containing hexose oxidase (Hox) (EC 1.1.1.5) from *Chondrus chrispus* expressed in *Hansenula polymorpha*.

TS-E 680™ (obtained from Danisco A/S) is a product containing fungal xylanase (EC 3.2.1.8) from *Aspergillus niger*.

TS-E 861™ (obtained from Danisco A/S) is a product containing fungal xylanase (EC 3.2.1.8) from *Aspergillus niger*, lipase (EC 3.1.1.3) from *Thermomyces lanuginosa* expressed in *Aspergillus oryzae*, and hexose oxidase (EC 1.1.1.5) from *Chondrus crispus* expressed in *Hansenula polymorepha*.

GRINDAMYL™ H 640 (obtained from Danisco A/S): contains bacterial xylanase

Grindamyl™ H 121 (obtained from Danisco A/S) is a fungal xylanase (EC 3.2.1.8) from *Aspergillus niger*.

Grindamyl™ EXEL 16 (obtained from Danisco A/S) is lipase (EC 3.1.1.3) from *Thermomyces lanuginosa* expressed in *Aspergillus oryzae*.

Grindamyl™ EXEL 66 (obtained from Danisco A/S) is a mixture of lipase (EC 3.1.1.3) from *Thermomyces lanuginosa* expressed in *Aspergillus oryzae* and a fungal xylanase (EC 3.2.1.8) from *Aspergillus niger*.

Lipopan F™ (Lipopan F BG) (obtained from Novozymes) is according to its producer (Novozymes) a purified lipolytic enzyme from *Fusarium oxysporum* produced by submerged fermentation of a genetically modified *Aspergillus oryzae* microorganism. According to its producer, Lipopan F has inherent activity toward phospholipids, glycolipids and triglycerides.

Recipes/Procedures
High Volume Tweedy
Recipe

| Product Name | % | Gram | ppm |
|---|---|---|---|
| Ijsvogel flour | | 3000 | |
| Water | 58 | | |
| Salt | | 60 | |
| Compressed yeast | | 180 | |
| Ascorbic acid | | | 30 |

Procedure:

Dough temperature: 29° C. (dough temp.–flour temp.+4° C. water temp.)

Mixing: 55 WH no vacuum

Resting: 5 min. at room temperature

Scaling: 500 g (bread), 1350 g (rolls)

Resting: 5 min. at room temperature

Moulding: Puma I 13 II 18 (bread), Fortuna 3/17/7 (rolls), Glimek (moulding machine) 1:4, 2:3, 3:12, 4:14

Proofing: 70 min. at 43° C., 70% RH. (bread), 50 min. at 34° C., 85% RH. (rolls)

Baking: BAGO, 35 min.+5 min. with the steamer open at 220° C., 12 sec. steam (bread), 17 min. at 220° C., 17 sec. steam (rolls)

Turkish Batard
Recipe

| Product name | % | Gram | ppm |
|---|---|---|---|
| Ijsvogel flour | | 2000 | |
| Water | 57,00 | | |
| Compressed yeast | | 80 | |
| Salt | | 30 | |
| Ascorbic acid | | | 70 |

Procedure:

Flour temperature: 15–17° C. (for trials—storage day before use at 15° C.)

Mixing: 35 min. After 25 min. add salt

After 30 min. add yeast

Dough temp.: 23–25° C.

Resting: 30 min. Bulk rest on table (table=22° C. & 80% RH)

Scaling 300 g. pieces

Rounding: By hand

Resting: 25 min. on table (table=22° C. & 80% RH) . . . start clock when scaling starts Molding=Glimek: 1:5, 2:4, 3:15, 4:10 . . . 10 in innerpos.

Proofing: 60 min. & 90 min. for this trial at 30° C. & 85% RH

Shock test

Baking: 20 min. in Bago1 & 25 min. in Bago2 . . . the last 5 min. is with the damper open for both ovens.

Bago1: 250° C. start temp. 5 sec. steam with damper open. Oven temp. down to 230° C. at once. Close damper after 11% min.

Bago2: 275° C. start temp. 8 sec. steam with damper open. Oven temp. down to 260° C. at once. Close damper after 11% min.

Crispy Rolls

Recipe:

| Product Name | % | Gram | ppm |
|---|---|---|---|
| Danish silver flour | | 2000 | |
| Water | 58/60 | | |
| Compressed yeast | | 120 | |
| Salt | | 32 | |
| Sugar | | 32 | |
| Ascorbic acid | | | 40 |

Procedure:

Mixing: Diosna 2+5 min. (depending on flour)

Dough temperature: 26° C.

Scaling: 1350 g

Resting: 10 min. at 30° C. in heating cabinet

Moulding: Fortuna 3/17/7

Proofing: 45 min alternatively 90 min at 34° C., 85% RH.

Baking: 18 min. at 220° C., 8 sec. steam (Bago-oven), 7 sec. steam (Wachtel-oven)

(MIWE program 28) (0.35 liter steam, 15 min. at 2000° C., ½ min. at 2200° C.)

US Toast

Here a sponge as a pre-mix is prepared, to all of which is then added the dough.

Recipe

| | | Gr | % |
|---|---|---|---|
| US Sponge: | Flour | 900.000 g | 50.000% |
| | Water | 900.000 g | 50.000% |
| | Dry Yeast | 23.400 g | 1.300% |
| | Yeast Food | 5.400 g | 0.300% |
| | Enzyme Complex | 0.054 g | 0.003% |
| | ADA | 0.036 g | 0.002% |
| US Dough: | Flour | 900.000 g | 50.000% |
| | Water | 234.000 g | 13.000% |
| | Dry Yeast | 25.200 g | 1.400% |
| | Sugar | 153.000 g | 8.500% |
| | Salt | 43.200 g | 2.400% |
| | Shortening (fat) | 36.000 g | 2.000% |
| | Sod.Prop. | 8.100 g | 0.450% |
| | Dimodan SDM-T (P100/B) | 9.000 g | 0.500% |
| | Asc. Acid. | 0.072 g | 0.004% (=7,200 g to 1000 ml. Take 10 ml. from the solution) |

Total flour amount: 1.800,000 g.

| Datem 22-CA-60 | 4.500 g | 0.2500% |
|---|---|---|
| S685 | 300 PPM | |
| H640 | 20 PPM | |
| TS-E 662 | 100 PPM | |

Care has to be taken with the water amount added from asc. acid solution and other water based solutions ex. enzymes.

The extra added water amount should be be withdrawn from the water amount on the Dough-side of the recipe.

The enzyme complex is a mix of alpha amylase and amyloclucosidase.

DIMODAN SDM-T (P100/B) (obtained from Danisco A/S) is a distilled monoglyceride.

Procedure:

| For the Sponge: | |
|---|---|
| Water Temp.: Hobart mixer | 25° C. |
| Step 1, | 1 min. |
| Step 2, | 1 min. |
| Step 3, | 1 min. |

Fermentation: 2 h & 15 min. 40° C. & 80% RH (relative humidity) 45 min. in freezer.

For the Dough:

Mix all ingredients together

Diosna-Mixer: Speed 1, 120 secs & Speed 2, 450 secs (or 28 degrees dough temp.)

On table—rest 5 min.

Weigh out the breads at 450 g pr. bread—rest 5 min.

Glimek (moulding machine) adjustments: 1, 2, 14, 11—& 9 cm—read on outer position.

Fermentation:

1 h & 10 min. 45 degrees Celsius & 90% RH

Bake-off:

Start temp.=250 degrees Celsius in 25 min.

Insert the breads and adjust bake-off temperature to 200 degrees Celsius at once.

Baking Trials

In each trial the dough characteristic, stickiness and all over bread score have been evaluated. The dough characteristic is a total of three different parameters: dough extensibility evaluated just after mixing and again after resting and stickiness after resting. Each parameter has been evaluated by bakers on a scale from 1–10, where 10 are the best. The score in the examples are a total of these different scores.

Stickiness evaluation has been subjectively evaluated by bakers just after mixing on a scale from 1 to 10, where 10 is the best, meaning non sticky.

All over bread score is a total of an evaluation made on bread crust, -crumb, possible capping and all over energy of the bread. Again each parameter is evaluated on a scale from 1–10, where 10 is the best.

EXAMPLE 7

Testing Alternatives in Tweedy Bread (UK Procedure)

The breads were rested for 70 min each and after a full proofing, each bread was shock treated in order to evaluate the shock resistance and thereby the dough stability.

In the baking trials, both pure enzyme solutions and combinations of DATEM and enzymes were tested as alternative to Lipopan F.

Baking Trials 4969-29

| Test | Specific volume, ccm/g | Shocked volume, ccm/g | Dough characteristic | Dough stickiness | All over bread score |
|---|---|---|---|---|---|
| 0.4% PANODAN GB | 5.6 | 4.64 | 15 | 4 | 29 |
| 0.2% PANODAN GB, 100 ppm GRINDAMYL H121, 100 ppm TS-E 662 | 5.75 | 4.92 | 14 | 4 | 30 |
| 100 ppm TS-E 662, 100 ppm GRINDAMYL H121, 100 ppm GRINDAMYL EXEL 16 | 5.57 | 4.47 | 14 | 4 | 20 |
| 40 ppm Lipopan F | 5.7 | 4.6 | 13 | 4 | 29 |
| 0.2% PANODAN GB, 20 ppm Lipopan F | 5.88 | 4.6 | 14 | 4 | 27 |
| 20 ppm Lipopan F, 100 ppm TS-E 662, 100 ppm GRINDAMYL H121 | 5.65 | 4.78 | 14 | 4 | 29 |
| 40 ppm Lipopan F, 100 ppm TS-E 662, 100 ppm GRINDAMYL H121 | 5.79 | 4.82 | 13 | 4 | 29 |

From the results it can be concluded that PANODAN GB results in a better crust of the product and a product.

The combination of PANODAN GB in combination with xylanase and hexose oxidase yields a beneficial effect.

When using DATEM and/or HOX in combination with GRINDAMYL EXEL 66 the volume is increased significantly and the crust is considerably improved. The test with 0.1% PANODAN GB 100 ppm GRINDAMYL EXEL 66 and 100 ppm TS-E 662 (HOX), gave a significantly good result at the same level as 0.4% PANODAN GB. Use of DATEM clearly gives a significantly positive effect on the crust as compared to pure enzyme solutions.

EXAMPLE 8

Testing Alternatives in Turkish Batard

Baking Trials 7258-2

| Test | Specific volume, ccm/g | Dough characteristic * | Dough stickiness ** | All over bread score*** |
|---|---|---|---|---|
| 15 ppm Lipopan F, 60 ppm TS-E 680 | 5.01 | 14 | 4 | 33 |
| 40 ppm Lipopan F | 3.78 | 15 | 5 | 32 |
| 100 ppm TS-861* | 5.03 | 16 | 5 | 44 |

* A combination of fungal xylanase, 1,3 triglyceride degrading lipase and hexose oxidase.

Both from the specific volume in the table as well as the pictures shown in FIGS. 1–3 it can be concluded that TS-E 861 performs better.

EXAMPLE 9

Testing Alternatives in Crispy Rolls

The rolls were fermented at two different fermentation times—45 and 90 min in order to stress the system and thereby give a better picture of the dough strengthening effect of the products. In general it can be said that 90 min of fermentation for a small crispy roll is quite long.

Baking Test: 4969-28

| Test | Specific volume 45 min, ccm/g | Specific volume 90 min, ccm/g | Dough characteristic * | Dough stickiness ** | All over bread score *** |
|---|---|---|---|---|---|
| 0.3% PANODAN A2020 | 7.15 | 8.48 | 14 | 5 | 25 |
| 30 ppm Lipopan F | 6.83 | 8.1 | 14 | 4 | 26 |
| 100 ppm TS-E 662, 100 ppm GRINDAMYL H121, 100 ppm GRINDAMYL EXEL 16 | 6.98 | 8.98 | 14 | 5 | 27 |

From the results it can be seen that use of the combination of xylanase, 1,3 triglyceride degrading lipase and hexose oxidase produces beneficial results.

In short fermentation times (45 min.) at certain concentrations PANODAN A2020 and Lipopan F gave comparable volume results. However, 0.3% PANODAN A2020 showed better results with regard to crispiness of the crust and a better dough stability in general. We found that Lipopan F often gave a slightly more "wet" crust.

Using HOX in combination with GRINDAMYL EXEL 66 and PANODAN 660 results in an increase in dough stability.

With prolonged fermentation times (90 min.) all buns become relatively unstable. At some concentrations PANODAN A2020 does, however, give the best result.

EXAMPLE 10

Testing Alternatives in US Toast

Test of Lipopan F in a US sponge and dough using flour from Mexico—hard wheat type. The breads have all been fully proofed and after that each bread have been shock treated in order to evaluate the shock resistance and thereby the dough stability.

Baking Trials 7230-1:

| Test | Specific volume, ccm/g | Shocked volume, ccm/g |
|---|---|---|
| 0.5% PANODAN 521 | 6.88 | 5.47 |
| 10 ppm Lipopan F | 6.16 | 5.36 |
| 20 ppm Lipopan F | 6.44 | 5.30 |
| 40 ppm Lipopan F | 6.28 | 5.52 |
| 0.25% PANODAN 521, 20 ppm GRINDAMYL H 640, 100 ppm TS-E 662 | 7.15 | 5.74 |

From these tests it is clear that the use of Hox results in a far better dough stability and consequently an increase of volume.

All publications mentioned in the above specification are herein incorporated by reference. Various modifications and variations of the described methods and system of the present invention may be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the claims.

Summary Paragraphs

Some aspects of the present invention are now described by way of Summary Paragraphs.

1. A method of improving the rheological properties of a flour dough and the quality of the finished product made from the dough, comprising adding to the dough ingredients, dough additives or the dough an effective amount of an oxidoreductase which is at least capable of oxidizing maltose.

2. A method according to paragraph 1 wherein the oxidoreductase is hexose oxidase.

3. A method according to paragraph 2 wherein the hexose oxidase is derived from a source selected from an algal species, a plant species and a microbial species.

4. A method according to paragraph 3 wherein the hexose oxidase is derived from *Chondrus crispus*.

5. A method according to paragraph 2 wherein hexose oxidase is added in an amount which is in the range of 1 to 10,000 units per kg of flour.

6. A method according to paragraph 5 wherein the hexose oxidase is added in an amount which is in the range of 10 to 1000 units per kg of flour.

7. A method according to paragraph 1 or 2 wherein the resistance to extension of the dough in terms of the ratio between the resistance to extension (height of curve, B) and the extensibility (length of curve, C), i.e. the B/C ratio, as measured by the AACC method 54-10 is increased by at least 10% relative to that of an otherwise similar dough not containing oxidoreductase.

8. A method according to paragraph 1 wherein the finished product is bread.

9. A method according to paragraph 1 wherein the finished product is a noodle product 10. A method according to paragraph 1 wherein the finished product is an alimentary paste product.

11. A method according to paragraph 1 wherein at least one further enzyme is added to the dough ingredients, dough additives or the dough.

12. A method according to paragraph 11 wherein the further enzyme is selected from the group consisting of a cellulase, a hemicellulase, a xylanase, a starch degrading enzyme, a glucose oxidase, a lipase and a protease.

13. A dough improving composition comprising an oxidoreductase which is at least capable of oxidising maltose and at least one further dough ingredient or dough additive.

14. A composition according to paragraph 13 wherein the oxidoreductase is derived from a source selected from an algal species, a plant species and a microbial species.

15. A composition according to paragraph 14 wherein the oxidoreductase is hexose oxidase.

16. A composition according to paragraph 15 wherein the hexose oxidase is derived from *Chondrus crispus*.

17. A composition according to paragraph 13 which is a pre-mixture useful for preparing a baked product or in making a noodle product or an alimentary paste product.

18. A composition according to paragraph 13 which comprises an additive from the group consisting of an emulsifying agent and a hydrocolloid.

19. A composition according to paragraph 18 wherein the hydrocolloid is selected from the group consisting of an alginate, a carrageenan, a pectin and a vegetable gum.

20. A method of preparing a bakery product the method comprising preparing a flour dough to which is added an effective amount of an oxidoreductase which is at least capable of oxidising maltose, and baking the dough.

21. A method according to paragraph 20 wherein the specific volume of the bakery product is increased relative to an otherwise similar bakery product prepared from a dough not containing oxidoreductase.

22. A method according to paragraph 21 wherein the specific volume is increased by at least 20%.

23. A method according to paragraph 20 wherein at least one further enzyme is added to the dough.

24. A method according to paragraph 20 wherein the further enzyme is selected from the group consisting of a cellulase, hemicellulase, a xylanase, a starch degrading enzyme, a glucose oxidase, a lipase and a protease.

25. A method according to paragraph 20 wherein the oxidoreductase is hexose oxidase.

26. A method of preparing a flour dough-based food product, comprising adding to the dough an effective amount of a maltose oxidising oxidoreductase.

27. A method according to paragraph 26 wherein the oxidoreductase is hexose oxidase.

What is claimed is:

1. A method of improving the rheological and/or machineability properties of a flour dough and/or the quality of the product made from the dough, comprising adding to the dough a combination comprising a hexose oxidase and an emulsifying agent, wherein the emulsifying agent is a lipase.

2. A method according to claim 1 wherein the lipase comprises a triacylglycerol lipase, a galactolipase, or a phospholipase.

3. A method according to claim 1 wherein the hexose oxidase is isolated from a red algae.

4. A method according to claim 1 wherein the flour dough comprises flour, water and at least one further dough additive or ingredient.

5. A method according to claim 1 wherein the flour dough comprises flour, water and at least one further dough additive or ingredient and wherein the further dough additive or ingredient is selected from the group consisting of a vegetable oil, a vegetable fat, an animal fat, shortening, butterfat, glycerol, milk fat and a mixture thereof.

6. A method according to claim 1 wherein the flour dough comprises a hard flour.

7. A method according to claim 1 wherein the product is a bread product.

8. A method according to claim 1 wherein at least one further enzyme is added to the dough.

9. A method according to claim 1 wherein at least one further enzyme is added to the dough, and wherein the further enzyme comprises a xylanase, a cellulase, a hemicellulase, a starch degrading enzyme, a protease, a lipoxygenase, an oxidoreductase or a lipase.

10. A dough improving composition comprising a hexose oxidase and an emulsifying agent, wherein the emulsifying agent is a lipase.

11. A dough improving composition according to claim 10 wherein the lipase comprises a triacylglycerol lipase, a galactolipase, or a phospholipase.

12. A dough improving composition according to claim 10 wherein the lipase comprises a triacylglycerol lipase, a galactolipase, or a phospholipase and wherein the hexose oxidase is isolated from red algae.

13. A dough improving composition according to claim 10 wherein the dough improving composition comprises at least one further dough additive or ingredient.

14. A dough improving composition according to claim 10 wherein the dough improving composition comprises at least one further dough additive or ingredient and wherein the further dough additive or ingredient comprises a vegetable oil, a vegetable fat, an animal fat, shortening, butterfat, glycerol or milk fat.

15. A dough improving composition according to claim 10 wherein the dough improving composition comprises at least one further dough additive or ingredient and wherein the further dough additive or ingredient is a hard wheat flour.

16. A method of preparing a bread product comprising adding a dough improving composition according to claim 10 dough ingredients, dough additives or a dough hind baking the dough comprising the dough improving composition to obtain the bread product.

17. A dough improving composition according to claim 10 wherein at least one further enzyme is added to the dough improving composition.

18. A dough improving composition according to claim 9 wherein al least one further enzyme is added to the dough improving composition and wherein the further enzyme comprises a xylanase, a cellulase, a hemicellulase, a starch degrading enzyme, a protease, a lipoxygenase, an oxidoreductase or a lipase.

19. A method of improving the rheological and/or machineability properties of a flour dough comprising adding to the dough a dough improving composition of claim 10.

20. A method of improving the volume or a baked product made from a flour dough comprising adding to the dough a dough improving composition of claim 10.

21. A method of improving the rheological and/or machineability properties of a flour dough and/or the quality of the product made from the dough, comprising adding to the dough a combination comprising a hexose oxidase and a triacylglycerol lipase.

22. A method of improving the rheological and/or machineability properties of a flour dough and/or the quality of the product made from the dough, comprising adding to the dough a combination comprising a hexose oxidase and a galactolipase.

23. A method of improving the rheological and/or machineability properties of a flour dough and/or the quality of the product made from the dough, comprising adding to the dough a combination comprising a hexose oxidase and a phospholipase.

24. A method according to claim 1 wherein at least one further enzyme is added to the dough and wherein the further enzyme comprises a xylanase, an amylase or a mixture of a xylanase and an amylase.

25. A dough improving composition according to claim 1 wherein the hexose oxidase is isolated from red algae and wherein the red algae comprises *Iridophycus flaccidum, Chondrus crispus*, or *Euthora cristata*.

26. A dough improving composition of claim 10 wherein at least one further enzyme is added to the dough improving composition and wherein the further enzyme comprises a xylanase, an amylase or a mixture of a xylanase and an amylase.

27. A method according to claim 1, wherein the hexose oxidase is isolated from a red algae and wherein the red algae comprises *Iridophycus flaccidum, Chondrus crispus* or *Euthora cristata*.

28. A method of improving the rheological and/or machineability properties of a flour dough and/or the quality of the product made from the dough, comprising adding to the dough a combination comprising a hexose oxidase and an emulsifying agent; wherein said flour dough comprises flour, water and at least one further dough additive or ingredient; wherein said further dough additive or ingredient is selected from the group consisting of a vegetable oil, a vegetable fat, an animal fat, shortening, butterfat, glycerol, milk fat and a mixture thereof and wherein said further dough additive or ingredient is present in an amount from 1 to 5% by the weight of the flour component of the dough.

29. A method according to claim 28 wherein the emulsifying agent is a lipase.

30. A method according to claim 28 wherein the emulsifying agent is a lipase and wherein the lipase comprises a triacylglycerol lipase, a galactolipase, or a phospholipase.

31. A method according to claim 28 wherein the hexose oxidase is isolated from rod algae.

32. A method according to claim 28 wherein the flour dough comprises at least one further dough additive or ingredient.

33. A method according to claim 28 wherein the flour dough comprises at least one further dough additive or ingredient and wherein the further dough additive or ingredient is a hard flour.

34. A method according to claim 28 wherein the product is a bread product.

35. A method according to claim 28 wherein at least one further enzyme is added to the dough.

36. A method according to claim 28 wherein at least one further enzyme is added go the dough and wherein the further enzyme is selected from the group consisting of a xylanase, a cellulase, a hemicellulase, a starch degrading enzyme, a protease, a lipoxygenase, an oxidoreductase, a lipase and a mixture thereof.

37. A dough comprising a dough improving composition wherein said dough improving composition comprises a hexose oxidase, an emulsifying agent and a further dough additive or ingredient; wherein said dough comprises flour and water; wherein said further dough additive or ingredient is selected from the group consisting of a vegetable oil, a vegetable fat, animal fat, shortening, butterfat, glycerol, milk fat and a mixture thereof and wherein said further dough additive or ingredient is present in an amount of from 1 to 5% by weight of the flour component of the dough.

38. A dough according to claim 37 wherein the emulsifying agent is a lipase.

39. A dough according to claim 37 wherein the emulsifying agent is a lipase and wherein the lipase comprises a triacylglycerol lipase, a galactolipase, or a phospholipase.

40. A dough according to claim 37 wherein the hexose oxidase is isolated from red algae.

41. A dough according to claim 37 wherein the dough improving composition comprises at least one further dough additive or ingredient.

42. A dough according to claim 37 wherein the dough improving composition comprises at least one further dough additive or ingredient and wherein the further dough additive or ingredient is a hard wheat flour.

43. A dough according to claim 37 wherein at least one further enzyme is added to the dough ingredients, dough additives or the dough.

44. A dough according to claim 37 wherein at least one further enzyme is added to the dough ingredients, dough additives or the dough and wherein the further enzyme is selected from the group consisting of a xylanase, an amylase, a cellulase, a hemicellulase, a starch degrading enzyme, a protease, a lipoxygenase, an oxidoreductase, a lipase, and a mixture thereof.

45. A dough according to claim 37 wherein at least one further enzyme is added to the dough ingredients, dough additives or the dough and wherein the further enzyme includes a xylanase, an amylase or a mixture thereof.

* * * * *

UNITED STATES PATENT AND TRADEMARK OFFICE
CERTIFICATE OF CORRECTION

PATENT NO. : 6,936,289 B2
APPLICATION NO. : 10/260578
DATED : August 30, 2005
INVENTOR(S) : Torkil Steenholt Olsen et al.

It is certified that error appears in the above-identified patent and that said Letters Patent is hereby corrected as shown below:

On the Cover Page, under (*) Notice, insert the following text -- This patent is subject to terminal disclaimers.--

Column 35, line 46, the text "10 dough ingredients, dough additives or a dough hind" should read --10 to dough ingredients, dough additives or a dough and--.

Column 35, line 53, the text "wherein al least one further enzyme is added to the dough" should read -- wherein at least one further enzyme is added to the dough--

Column 36, line 48, the text "oxidase is isolated from rod algae." should read --oxidase is isolated from red algae.--.

Column 36, line 61, the text "further enzyme is added go the dough and wherein the" should read --further enzyme is added to the dough and wherein the--.

Column 37, line 5, the text "vegetable fat, animal fat, shortening, butterfat, glycerol" should read --vegetable fat, an animal fat, shortening, butterfat, glycerol--.

Signed and Sealed this

Twenty-third Day of October, 2007

JON W. DUDAS
*Director of the United States Patent and Trademark Office*